(12) United States Patent
Hoang et al.

(10) Patent No.: US 6,916,133 B2
(45) Date of Patent: Jul. 12, 2005

(54) PATIENT PREPARATORY APPLICATOR WITH A BACK PLUG ACTIVATOR

(75) Inventors: Minh Quang Hoang, Taylorsville, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/452,587

(22) Filed: Jun. 2, 2003

(65) Prior Publication Data

US 2004/0240927 A1 Dec. 2, 2004

(51) Int. Cl.[7] .......................... B43K 5/14; A61M 35/00
(52) U.S. Cl. .......................... 401/133; 401/132; 604/3
(58) Field of Search .......................... 401/132, 13, 134, 401/135; 604/3

(56) References Cited

U.S. PATENT DOCUMENTS

| | | | |
|---|---|---|---|
| 4,304,869 A | * 12/1981 | Dyke | 435/287.6 |
| 4,893,730 A | 1/1990 | Bolduc | 222/80 |
| 5,302,358 A | 4/1994 | Andersen et al. | 422/305 |
| 5,425,915 A | 6/1995 | Phillips et al. | 422/58 |
| 5,435,660 A | * 7/1995 | Wirt | 401/135 |
| 5,658,084 A | 8/1997 | Wirt | 401/132 |
| 5,791,801 A | 8/1998 | Miller | 401/132 |
| 6,371,675 B1 | 4/2002 | Hoang et al. | 401/205 |

* cited by examiner

Primary Examiner—David J. Walczak
(74) Attorney, Agent, or Firm—Mony R. Ghose

(57) ABSTRACT

An applicator having a substantially hollow body for accommodating an ampoule of solution. The hollow body comprises an open proximal end for receiving the ampoule and an open distal end having a flange to accept an applicator pad for applying the solution. A back plug having a lever mechanism is inserted into the open proximal end of the applicator to activate the applicator and seal the applicator after activation. Advancement of the back plug lever mechanism into the hollow body pivots the body of the ampoule to break the neck, activatiug the applicator. The back plug seals the proximal end after activation of the applicator.

26 Claims, 21 Drawing Sheets

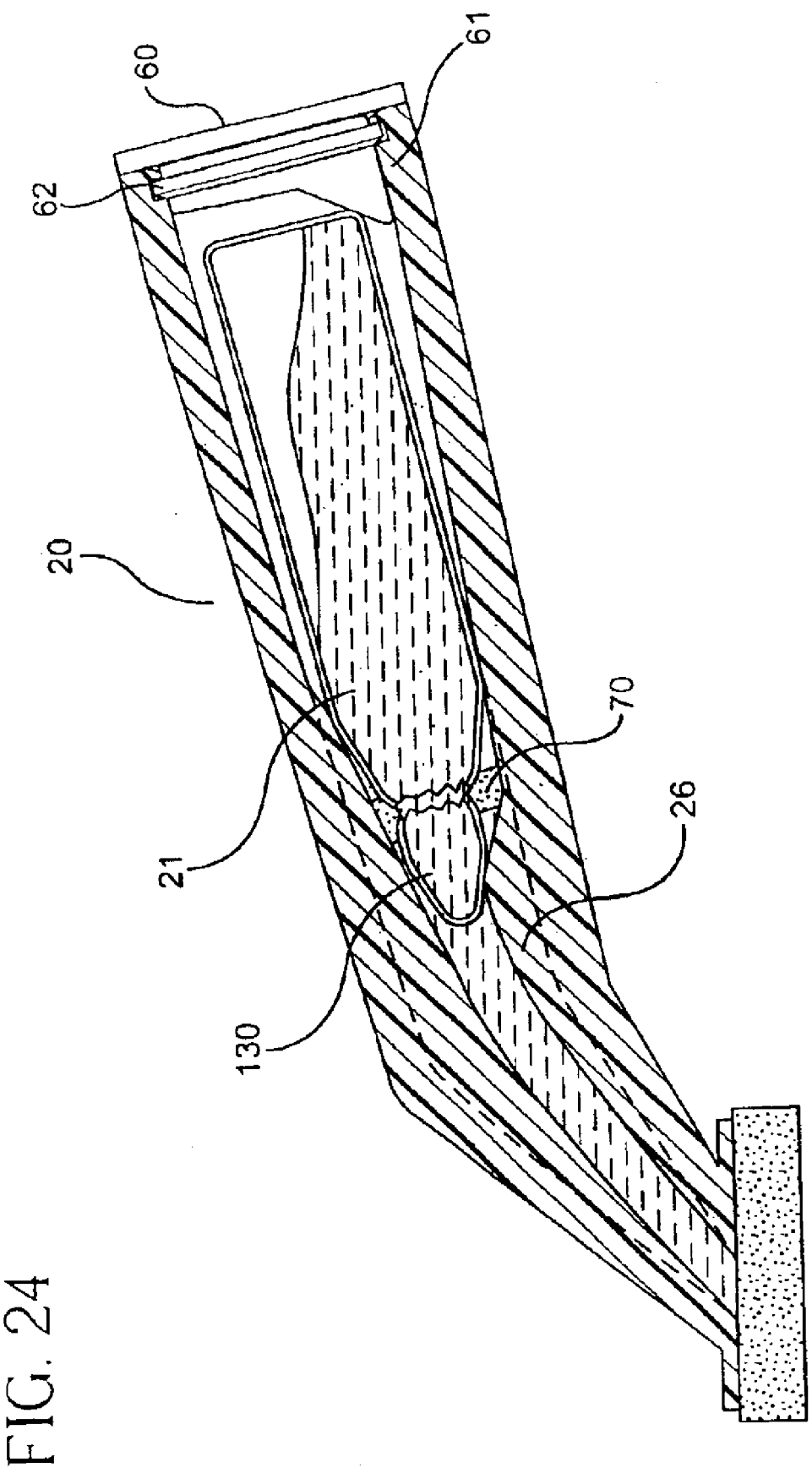

PATIENT PREPARATORY APPLICATOR WITH A BACK PLUG ACTIVATOR

FIELD OF THE INVENTION

The present invention relates to a device and method for applying an antimicrobial solution to a patient's skin and, more particularly, to an applicator that dispenses the antimicrobial solution from an ampoule when activated with a back plug.

BACKGROUND OF THE INVENTION

Because microorganisms lie on the skin, standard invasive medical procedures require a patient's skin, where the procedure is to take place, to be disinfected prior to the procedure. This skin preparation is important in order to minimize the risk of infection to the patient.

Alcohol has long been recognized as a fast acting broad-spectrum disinfectant. Alcohol-based prep solutions have many advantages over soap- or water-based prep solutions, such as reduced prepping and solution drying time. However, alcohol is flammable and its use and application on a patient should be carefully controlled in order to minimize the fire hazard created when such an alcohol-based prep solution is used. Indeed, in its January 1992 Guidance on Surgical Fires, the ECRI, (formerly the Emergency Care Research Institute) stated that approximately ten surgical patient fires come to its attention per year. These fires may ignite on or in the patient and may cause considerable injury to the patient. Today's surgical rooms, patient care facilities and procedures may utilize an increasing number of electrical equipment and devices. When this equipment and/or these devices are used in the vicinity of flammable solutions or vapors, the health care practitioner must be particularly careful to avoid such accidents. If alcohol-based solution is dispensed from an applicator having no flow control mechanism, in certain circumstances, the solution can flow excessively fast and "pool" up on the body, thereby increasing the potential hazard.

Additionally, subsequent to prepping, a patient is often covered with a surgical cloth drape. This drape may collect flammable vapors as any excess alcohol dries and vaporizes. This remaining alcohol vapor and/or liquid can then ignite with the addition of a significant heat source, such as electrosurgical or electrocautery units. Other ignition sources may include defibrillators, heated probes, drills and burs, argon beam coagulators, fiber optic light sources and cables and lasers used with the free-beam (bare-fiber) method. Often, this environment is made more combustible by the common use of oxygen in the surgical area, creating an oxygen rich atmosphere.

Many different antimicrobial applicators exist but could be improved. First generation applicators, as depicted in, for example, U.S. Pat. No. 4,183,684, allow the applicator contents to flow in large uncontrolled amounts. Other antimicrobial applicators that accommodate an ampoule that is broken for activation exist but could also be improved. One such type of applicator includes a lever mechanism on a side of the applicator wherein the lever mechanism is partially located within the applicator. When the lever mechanism is depressed, the internal portion of the lever applies pressure on the ampoule to break the ampoule and release the solution contained therein. Examples of applicators with external side lever mechanisms include U.S. Pat. No. 5,302,358 issued to Anderson et al. on Apr. 12, 1994; U.S. Pat. No. 5,425,915 issued to Phillips et al. on Jun. 9, 1995; and U.S. Pat. No. 6,371,675 issued to Hoang et al. on Apr. 16, 2002 each incorporated herein by reference. Other applicators provide a flexible portion of the applicator body at the location of the ampoule to break the ampoule and release the contents contained therein such as those disclosed in U.S. Pat. No. 4,893,730 issued to Bolduc on Jan. 16, 1990, U.S. Pat. No. 5,098,297 issued to Chari et al. on Mar. 24, 1992; and U.S. Pat. No. 5,791,801, each incorporated herein by reference.

These types of applicators are problematic because they may allow excessive amounts of the antimicrobial solution to flow onto the patient where it could pool and create a significant fire hazard if the antimicrobial solution is flammable. This is due in large part because both designs rely on gravity and the free flow of solution from the applicator to the foam application pads to dispense the applicator contents. As a consequence, if the applicator is not positioned to prevent solution flow, unwanted residual solution will continue to flow. In addition, even when the applicator is positioned to prevent solution flow, the free communication between the solution storage and the foam applicator allows fumes to continue to escape into the operating environment. Furthermore, a patient is often covered by a surgical cloth drape after prepping, i.e., the disinfecting procedure, takes place. When dispensation of the solution is not sufficiently controlled, a significant amount of the antimicrobial solution may collect on the surgical drape. Again, if the antimicrobial solution is flammable, a potential exists for an injury to the patient and the healthcare professionals in the area. Also, this inability to adequately control the flow of antimicrobial solution on and around the patient increases the likelihood that the solution will stain material in the area.

For user and patient safety, therefore, solution flow control is an extremely important characteristic of a skin prep applicator. A means to control flow is especially important for a skin prep applicator dispensing a flammable solution, such as an alcohol-based antimicrobial solution. The importance of flow control increases as the amount of dispensable solution increases.

More recently, applicators have been developed to control solution flow by customizing the applicator pads with slits of various numbers, such as in co-owned U.S. Pat. No. 6,371,675, which is incorporated herein by reference.

SUMMARY OF THE INVENTION

It is, therefore, an object of an implementation of the invention to provide an applicator for an antimicrobial solution that is easily activated and used as a single step applicator.

It is an object of another implementation of this invention to provide an applicator for an antimicrobial solution that allows the user to start and stop the flow of solution when desired.

It is yet another object of another implementation of the invention to provide an applicator for an antimicrobial solution that controls the rate at which the solution is dispensed from the applicator.

Still another object of another implementation of this invention is to provide an applicator for an antimicrobial solution that allows the solution to remain in the applicator after some of the solution has been dispensed for subsequent disposal.

It is still another object of another implementation of this invention to provide an applicator for an antimicrobial solution that allows the solution and its vapors to no longer communicate with the operating room environment when the solution dispensing mechanism is closed.

It is still another object of another implementation of this invention to provide an applicator for an antimicrobial solution that is capable of being sterilized with no adverse effects on the function of the applicator or the antimicrobial solution contained therein.

It is yet another object of another implementation of this invention to provide an applicator for an antimicrobial solution wherein the applicator provides a back plug to activate the flow of antimicrobial solution and to seal the applicator.

The above and related objects are realized by prep applicators in accord with aspects of the present invention. The applicator described herein is designed for use with a glass ampoule having a breakable neck. The applicator of the present invention preferably comprises a rigid applicator body, a flow controlling applicator pad assembly, a highly porous foam insert and a back plug to both break the ampoule and seal the applicator body. More particularly, certain implementations of the applicator of this invention include a tapered hollow body having a hollow handle portion. The hollow handle portion has an open proximal end and a distal end, which includes a flanged arm plate to receive an applicator pad. A back plug having a lever mechanism is inserted into the open proximal end of the hollow body to activate the flow of the antimicrobial solution from the ampoule to the applicator pad and then to the patient. A porous foam ring insert inside the hollow body around the neck portion of the ampoule promotes solution flow from the ampoule. An optional flow control feature is a slit formed in the applicator pad. The slit is designed so that it remains closed when no pressure is exerted on the distal surface of the applicator pad; however, when pressure is exerted on the distal surface of the applicator pad, such as when the applicator is pressed against a patient's skin, the slit opens to allow the antimicrobial solution to flow past the slit into the applicator pad. There the antimicrobial solution can be easily distributed over the patient's skin by the applicator pad. When a sufficient amount of the antimicrobial solution has flowed into the applicator pad, the user can release the pressure sensitive flow control slit to stop the flow of antimicrobial solution out of the applicator.

These and other objects and advantages of the present invention in its various implementations will become apparent from the subsequent detailed description of the preferred embodiment and the claims taken in conjunction with the accompanying drawings.

BRIEF DESCRIPTION OF THE DRAWINGS

The preferred embodiments are illustrated in the drawings in which like reference numerals refer to like elements and in which:

FIG. 24 is a side view of an example of an applicator illustrating sealing the applicator after activation;

DETAILED DESCRIPTION OF THE INVENTION

As used herein, the term "proximal" refers to a location on the applicator of the present invention that, during normal use, is closest to the clinician using the device and farthest from the patient in connection with whom the device is used. Conversely, the term "distal" refers to a location on the applicator of the present invention that, during normal use, is farthest from the clinician using the device and closest to the patient in connection with whom the device is used.

As used herein, the terms "top," "up" or "upwardly" refer to a location on the applicator of the present invention that, during normal use, is radially away from the device and away from the patient's skin. Conversely, as used herein, the terms "bottom," "down" or "downwardly" refer to a location on the applicator of the present invention that, during normal use, is radially away from the device and toward the patient's skin.

As used herein, the terms "in" or "inwardly" refer to a location with respect to the applicator of this invention that, during normal use, is toward the inside of the device. Conversely, as used herein, the terms "out" or "outwardly" refer to a location with respect to the applicator of this invention that, during normal use, is toward the outside of the device.

As used herein, the term "vertically" refers to the directional movement of the ampoule within the hollow handle, which, during activation, is toward an inside top side of the applicator of this invention.

As used herein, the term "axially" refers to the directional movement of the axially activated back plug along the axis of the applicator of this invention, that, during normal use, is toward the distal end of this applicator.

Although the applicator of this invention is described for use with an alcohol-based antimicrobial prep solution, it is to be understood that any liquid antimicrobial prep solution, whether alcohol-based or non-alcohol-based, may be used with this applicator.

The applicator of the present invention is a safe, single step and convenient hand-held prep applicator system containing a breakable ampoule filled with an antimicrobial solution. The applicator further includes a means for activation of the flow of solution, a solution flow control and a solution delivery means. The applicator also has a comfortable user and patient interface and provides for non-messy use and disposal.

Figure 1:
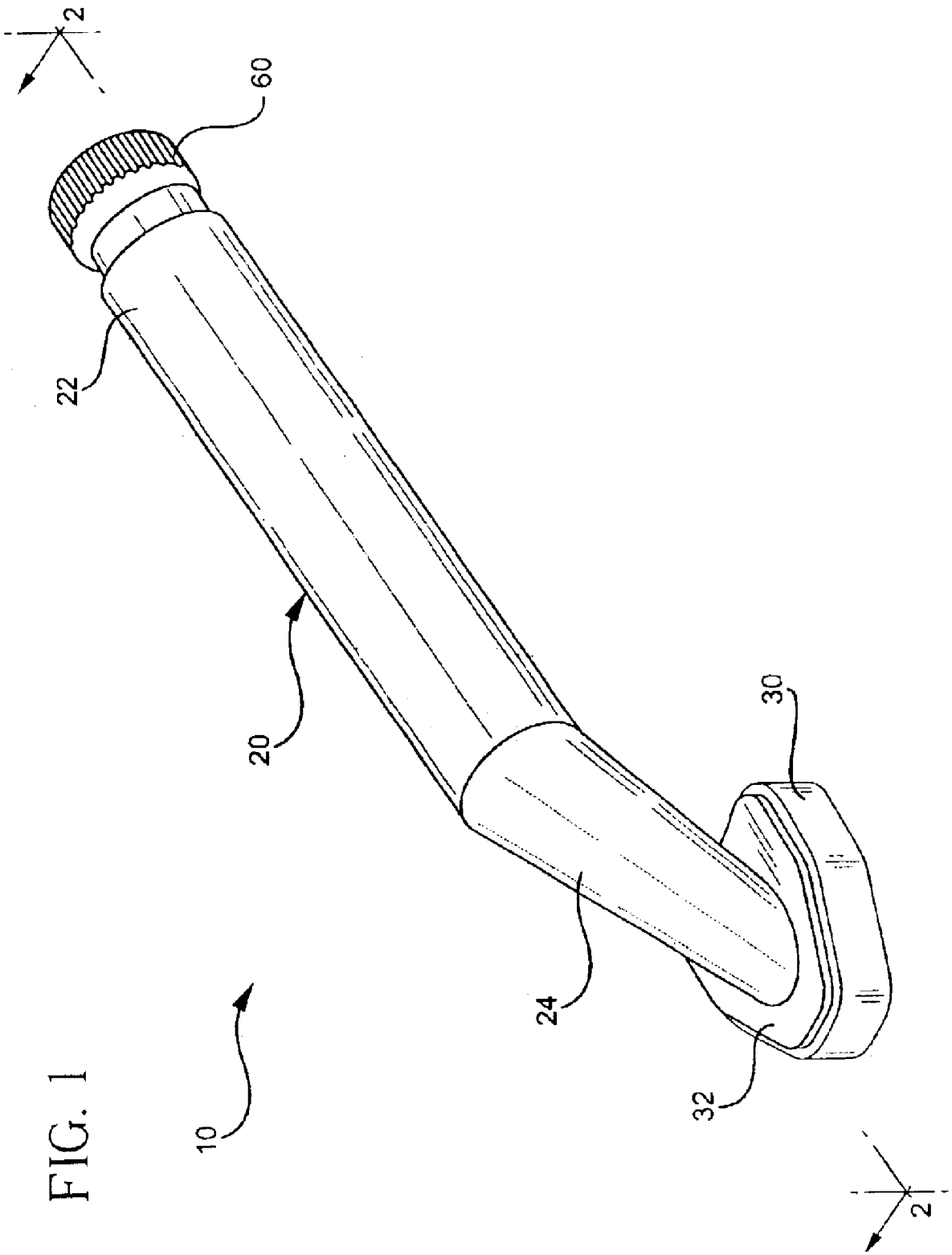
FIG. 1 is a perspective view of an applicator of this invention.
Figure 2:
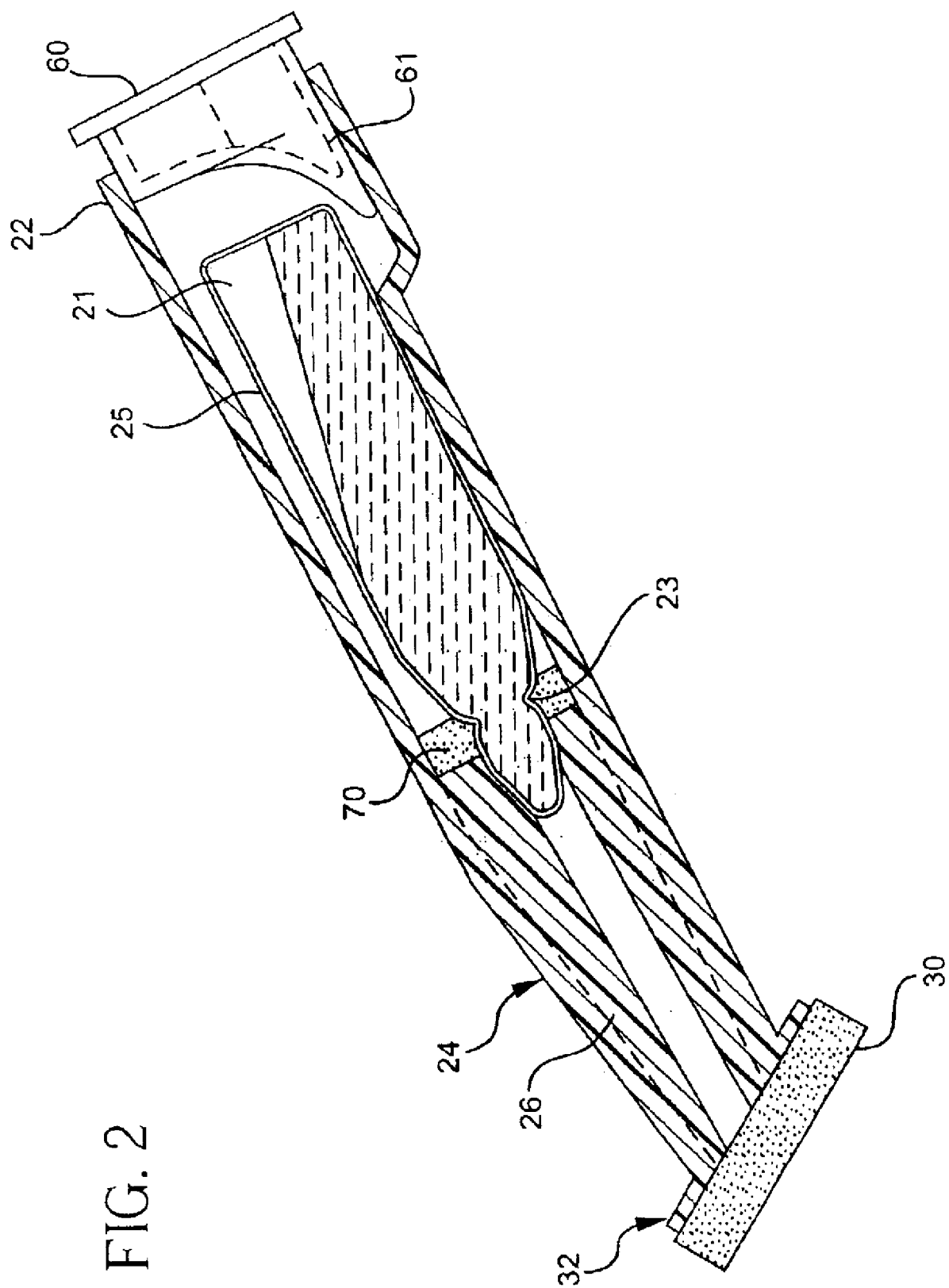
FIG. 2 is a side view of an example of the body of the applicator of this invention.
Figure 3:
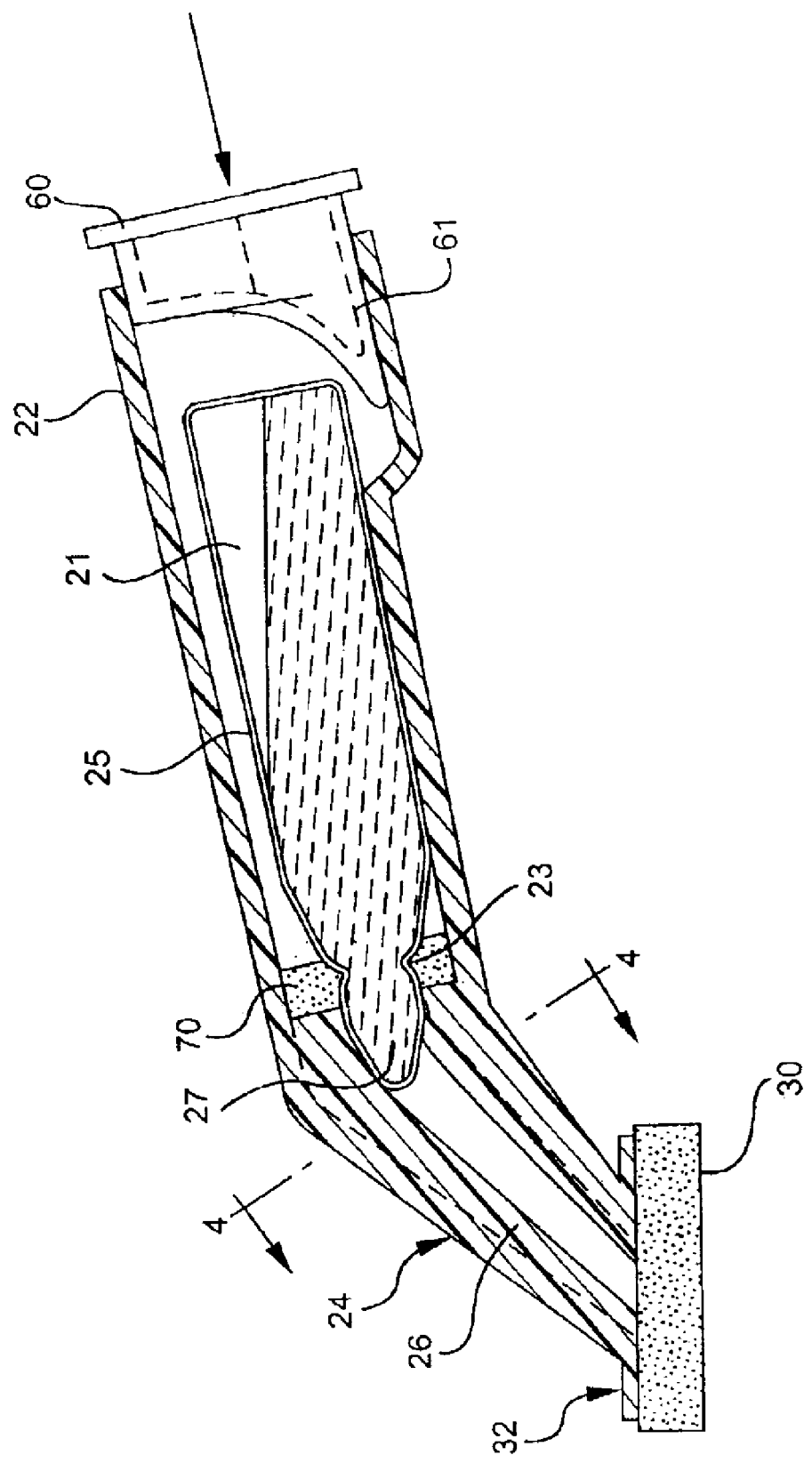
FIG. 3 is a side view of another example of the body of the applicator of this invention.

The applicator of the present invention is designed for use with an ampoule containing an antimicrobial prep solution. The ampoule has a breakable neck for discharging the antimicrobial prep solution contained therein. Referring now to FIG. 1, the applicator 10 includes a generally tapered rigid hollow body 20, a flow controlling applicator pad assembly 30 and a back plug 60, which acts as a means to break the ampoule and to seal the applicator hollow body 20 at the proximal end after activation. Hollow body 20 includes a handle portion 22 at a proximal end and includes a distal portion 24. The shape of hollow body 20 may be substantially straight, as illustrated in FIG. 2, or distal portion 24 may extend from handle portion 22 at an angle, as illustrated in FIG. 3. The diameter of handle 22 is increased at the proximal end to accommodate a lever mechanism 61 of back plug 60. Prior to activation, back plug 60 is partially inserted into hollow body 20 and an end of lever mechanism 61 is positioned under ampoule 25.

Referring to the applicator of FIG. 2, the interior diameter of hollow body 20 at the handle portion 22 is sufficient to accommodate the body 21 of ampoule 25 and to allow for sufficient movement of ampoule body 21 at its proximal end to break neck 23 of ampoule 25. Open cell foam ring 70 located inside applicator 10 approximately between handle portion 22 and distal portion 24 surrounds neck 23 of ampoule 25. The interior surface of the distal portion 24 of hollow body 20 includes a structure to firmly hold the ampoule head 27 rigid and to allow the solution to flow through the structure to applicator pad 30 after activation. The structure illustrated includes ribs 26 that are parallel with the hollow body 20. Alternative structures include a conduit or mesh. The ring 70 may be made of any wicking material.

Figure 4:
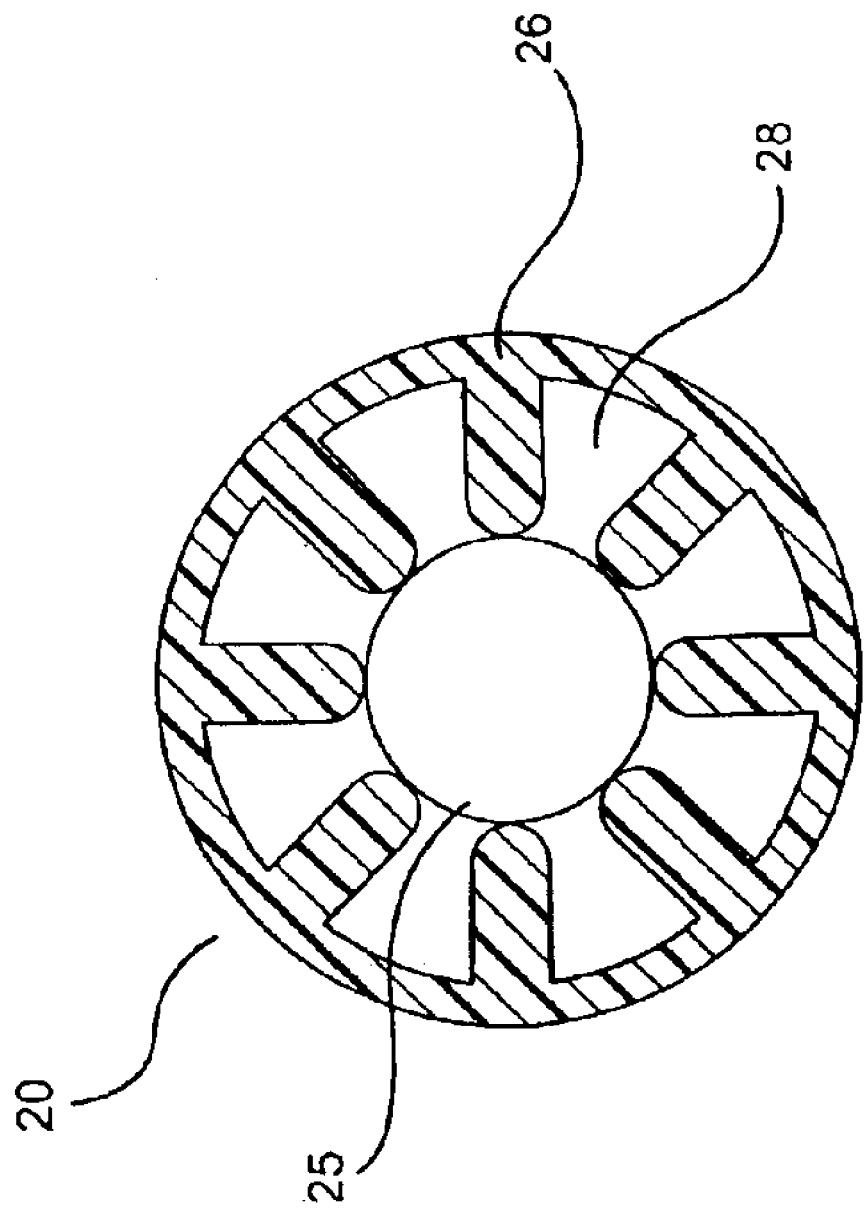
FIG. 4 is a cross sectional view of the applicator of the present invention illustrating an example of a structure to hold the ampoule firmly in place.

The interior area 28, or columns, between ribs 26 provides passage for the antimicrobial solution dispensed from ampoule 25 (after the ampoule is broken) and into the distal end of applicator 10 to applicator pad 30. FIG. 4 is a cross sectional view of hollow body 20 illustrating ribs 26 that hold ampoule 25 firmly in place and the area between the ribs that provides passage for solution dispensed from the ampoule. FIG. 3 is a side view of applicator 10 containing ampoule 25 to illustrate the contact between ribs 26 and head 27 of ampoule 25 that holds head 27 firmly in place for activation. Alternatively, ribs 26 may be extended a distance into handle portion 22 to contact body 21 of ampoule 25 to hold ampoule 25 more firmly in place and to change the pivot point to achieve the desired or required force to break neck 23 of ampoule 25.

Figure 5:
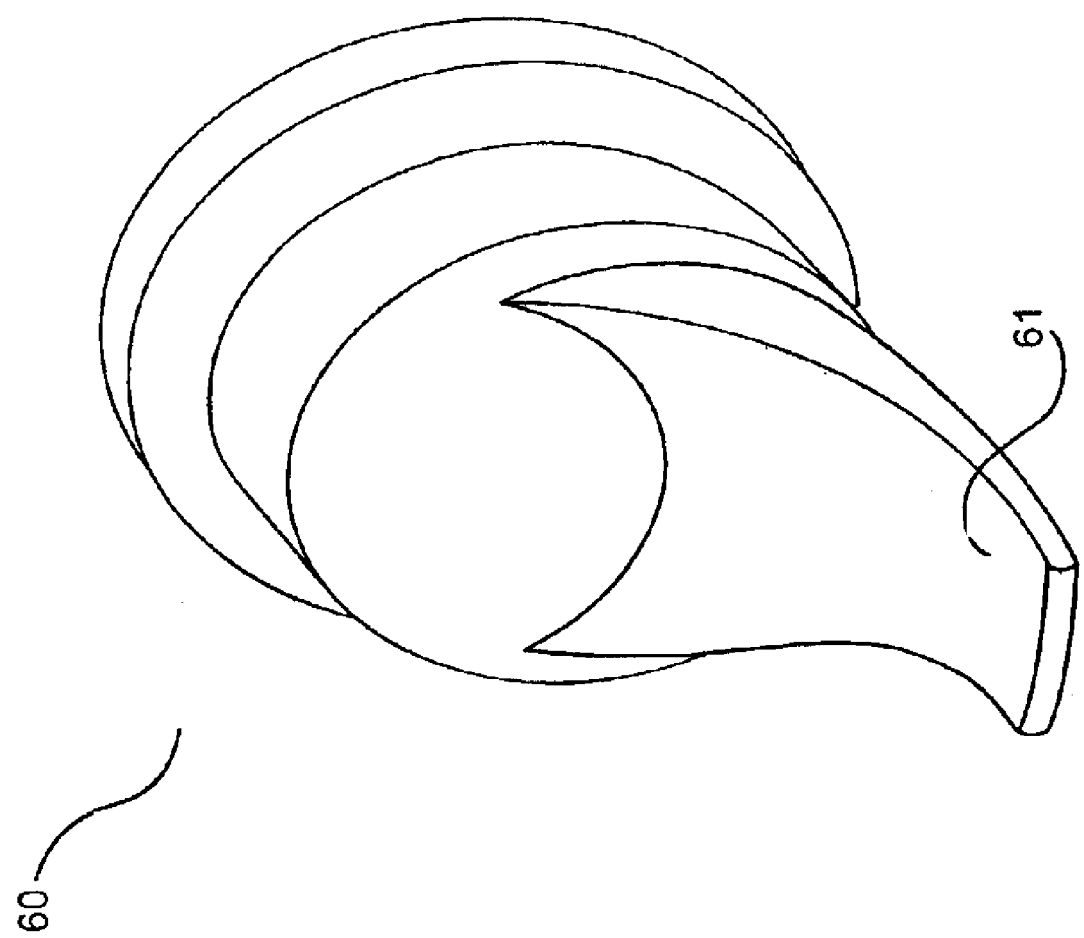
FIG. 5 is a perspective view of an axially activated back plug.

The activation of this type of applicator involves breaking the ampoule containing the antimicrobial solution. This can be done by a variety of means involving an internal lever mechanism. Back plug 60 includes internal lever mechanism 61, which may be a wedge, for activating applicator 10, as illustrated in FIG. 5. When back plug 60 is advanced into hollow body 20, internal lever mechanism 61 causes ampoule 25 to pivot, thereby breaking ampoule 25 at its weak point. The ampoule weak point is in the neck portion because of "scored" glass around the circumference of ampoule 25. To facilitate breakage, the ampoule's head 27 must be sufficiently and firmly held in the applicator body 20 and have a score line therein. Additionally, in order to facilitate activation of the applicator of this invention, the wall thickness of the applicator hollow body 20 and ribs 26 near the head portion 27 of ampoule 25 should be sufficiently thick to hold the head portion 27 firmly in place during activation. The ampoule must also be sufficiently strong to prevent pre-mature activation during processing, shipping and handling.

An open cell foam ring insert 70 having a high porosity is placed inside applicator hollow body 20 around neck portion 23 of ampoule 25. This foam ring insert is held in place by hollow body 20 and ampoule 25. In prior art applicators, when the ampoule was broken, the surface tension prevented the solution in the ampoule from flowing out of the ampoule. Foam ring insert 70 is provided in the present applicator 10 to promote flow of the antimicrobial solution from ampoule 25. The ampoule is inserted into handle portion 22 of applicator 10 at the open proximal end. Ampoule 25 is held in place at the head 27 by ribs 26, which are inside and parallel to applicator body 20. Foam ring 70 promotes flow of the solution from ampoule 25, while ribs 26 allow the solution to flow into the distal portion after the ampoule is broken.

Back plug 60 is advanced into the proximal end of applicator handle portion 22 for activation. Back plug 60 includes a lever mechanism for pivoting the body of the ampoule to break its neck. Various configurations of back plug 60 may be used to activate the applicator of the present invention. For example, the back plug may be advanced by applying an axial force to a press fit back plug, which advances the internal lever mechanism within the hollow body, or the back plug may be rotationally advanced into the hollow body. The configuration of the internal lever mechanism of the back plug corresponds to the axial or rotational configuration of the back plug. The back plug acts on the proximal-most portion of the ampoule, thereby increasing the length of the lever arm through which the delivery force to be the distance from the neck to the proximal end of the ampoule. In any event, it is desirable that the back plug is designed such that, as it is displaced, the ampoule is displaced, thereby breaking the ampoule, and causing fluid flow.

Figure 6:
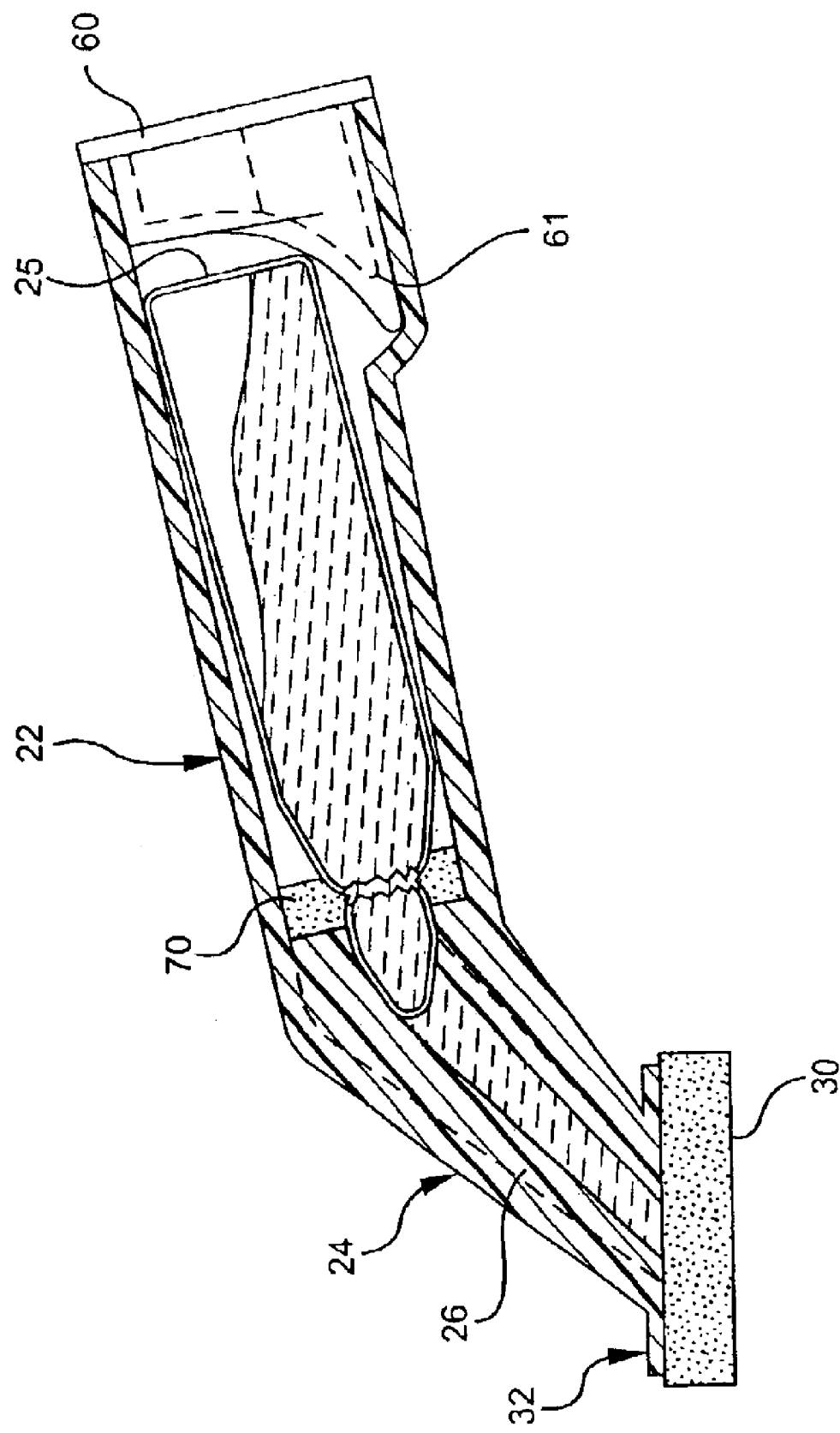
FIG. 6 is a side view of an example of the applicator of this invention after activation.
Figure 7:
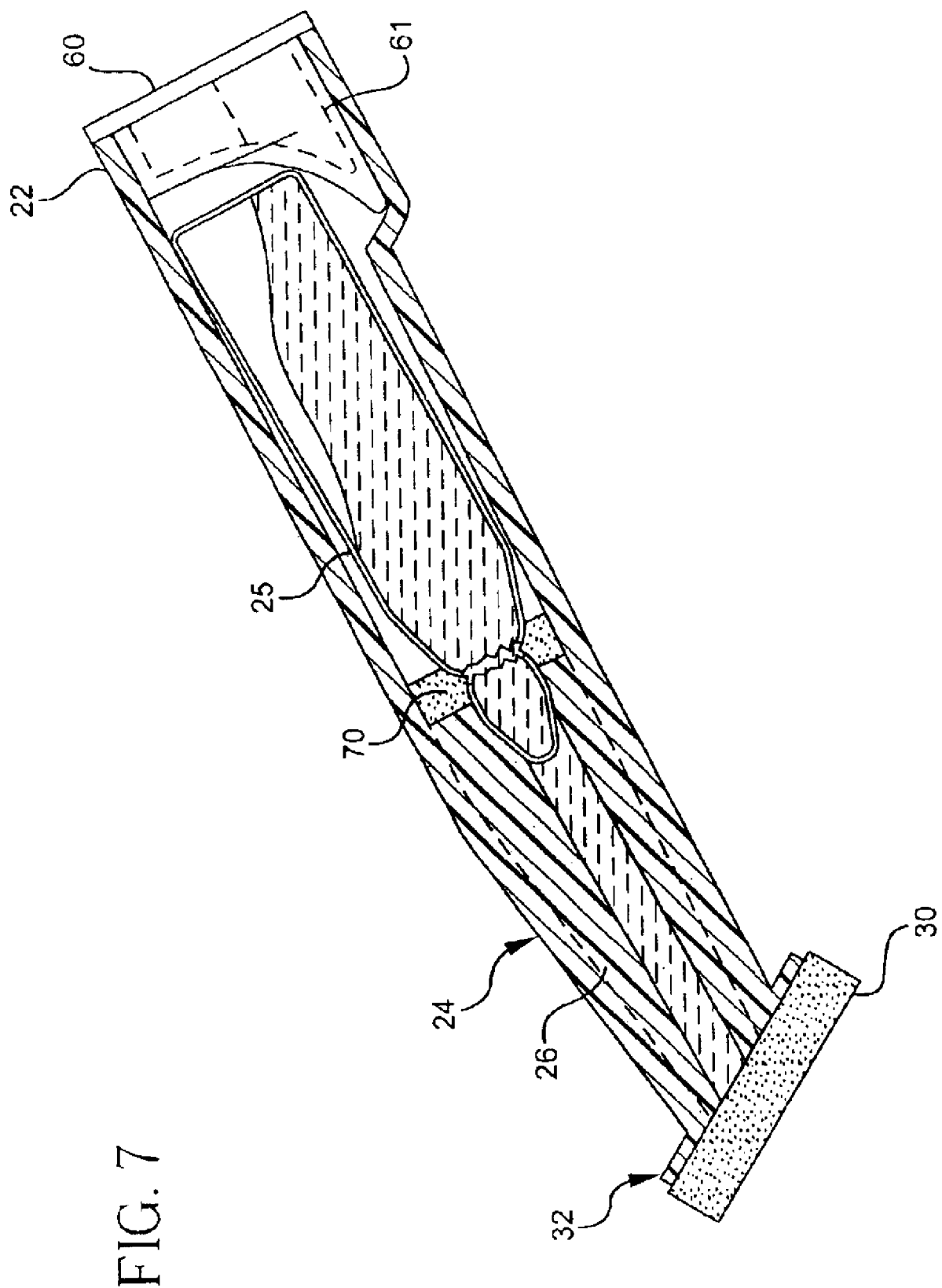
FIG. 7 is a side view of another example of the applicator of this invention after activation.

Referring now to FIG. 2, the applicator of the present invention may be activated by axially pressing back plug 60 into the open proximal end of applicator hollow body 20. Pressure may be applied to back plug 60 by a user's hand or by pressing the applicator and partially inserted back plug 60 against a rigid surface. When axially advanced back plug 60 is pressed into the opening at the proximal end of applicator 10, internal lever mechanism 61, which may be wedge-shaped, advances under the ampoule to pivot ampoule 25, as illustrated in FIGS. 6 and 7, to break the neck, thereby activating applicator 10. Internal lever mechanism 61 may include a concave surface to accommodate ampoule 25 and to position ampoule 25 for movement in the vertical direction.

Figure 8:
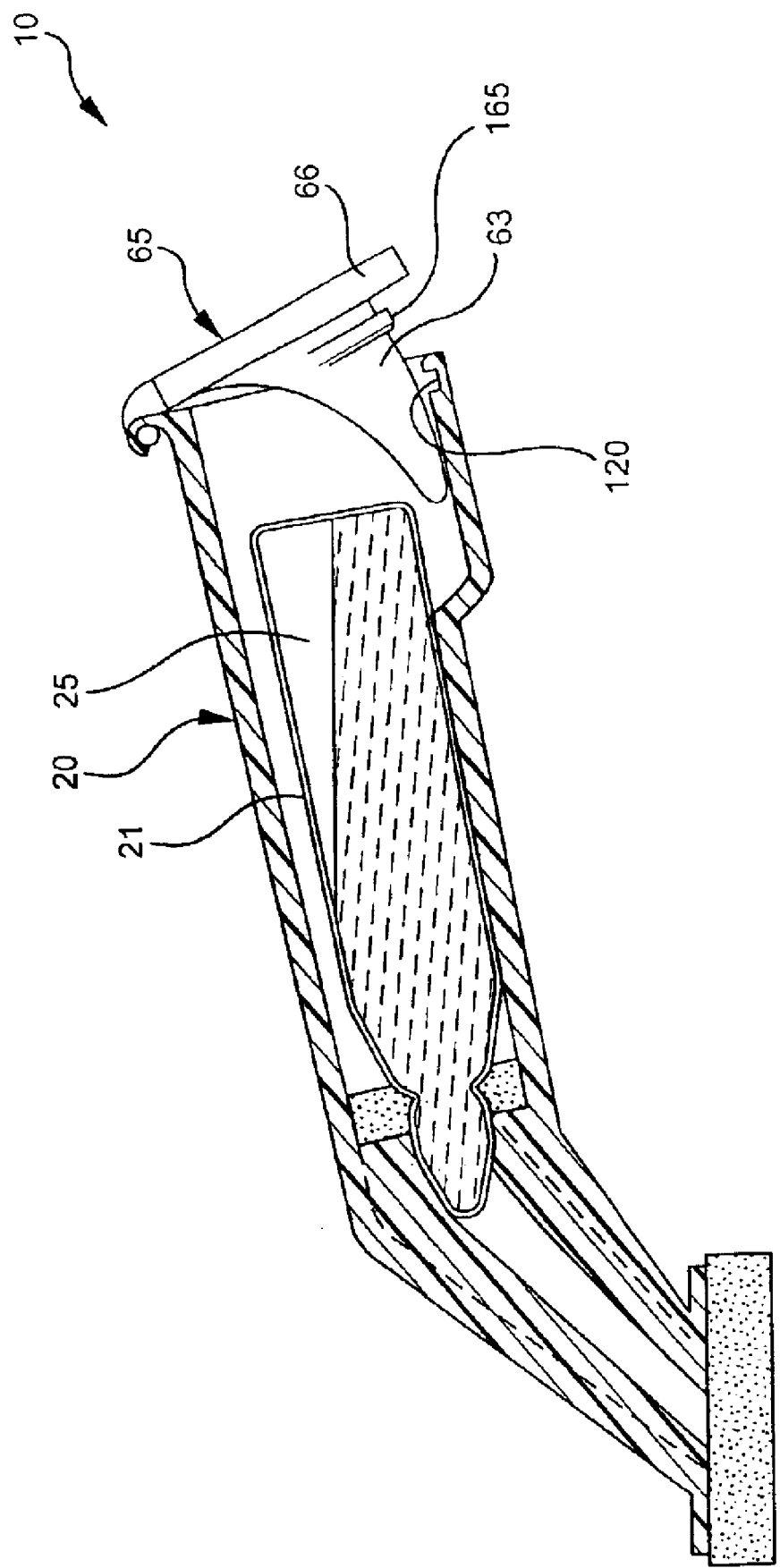
FIG. 8 is side view of the applicator having a back plug pivotally connected with the body of the applicator of this invention.

Axially advanced back plug 60 may alternatively be pivotally connected with the proximal end of the applicator, as illustrated in FIG. 8. As seen therein, pivotal back plug 65 includes a lever arm 66, which rotates downwardly to push internal lever 63 into applicator 10. Lever arm 66 is of sufficient length to allow the user to activate the applicator with less force. A longer length requires an increased displacement of the lever arm and reduces the force required to advance the back plug 60 into the hollow body. Internal lever 63 of pivoting back plug 65 functions in the same manner as lever mechanism 61 of axially activated back plug 60. When the back plug is fully advanced, rib 165 of the back plug becomes seated in groove 120 in the body 20, preferably sealing the proximal end of the body and preventing opening of the plug after actuation. This means for maintaining the back plug in place prevents any portion of the broken ampoule or remaining solution from exiting the proximal end of the body.

Figure 9:
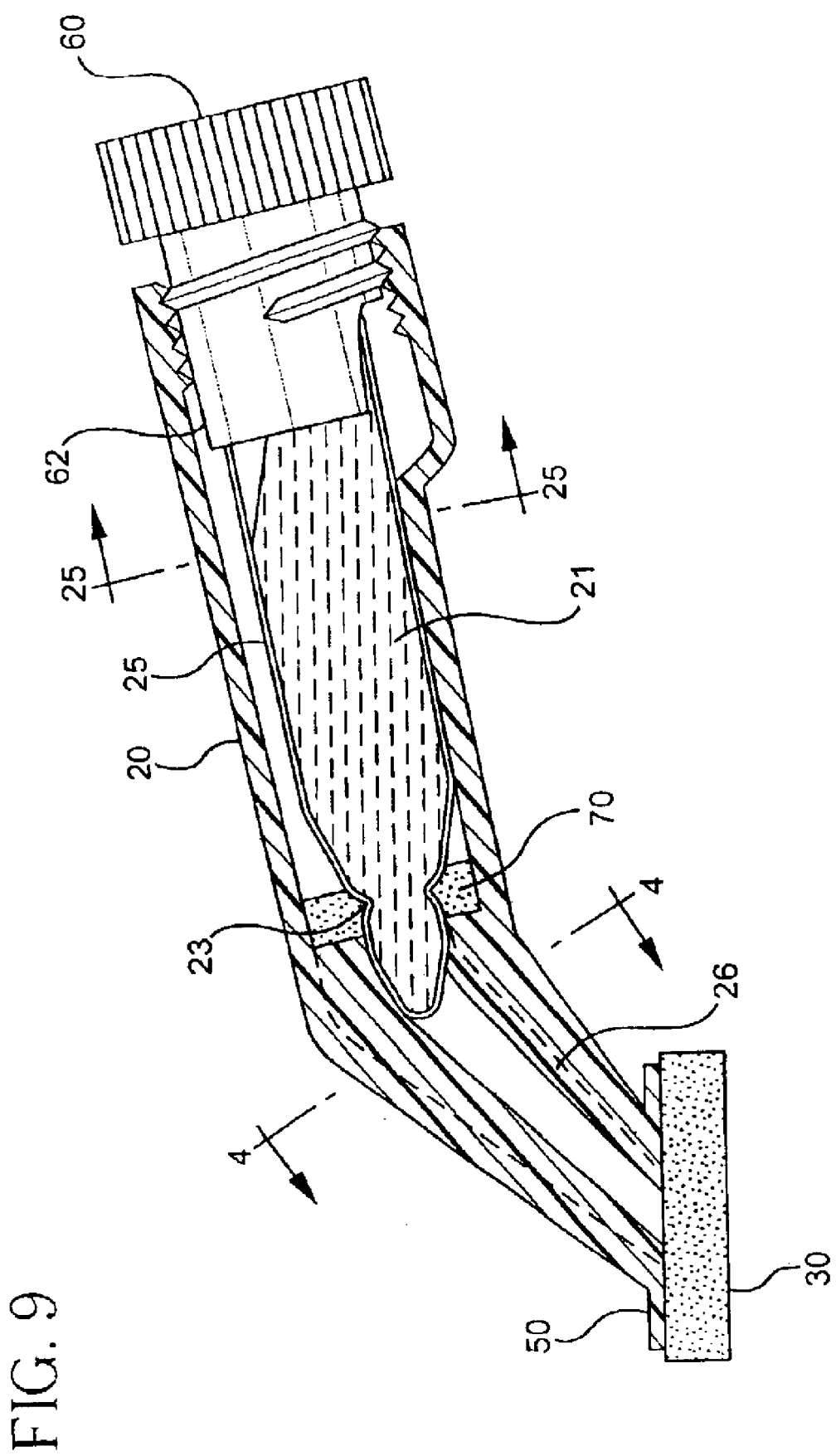
FIG. 9 is a side view of an example of the applicator of the present invention with a rotationally activated back plug prior to activation.
Figure 10:
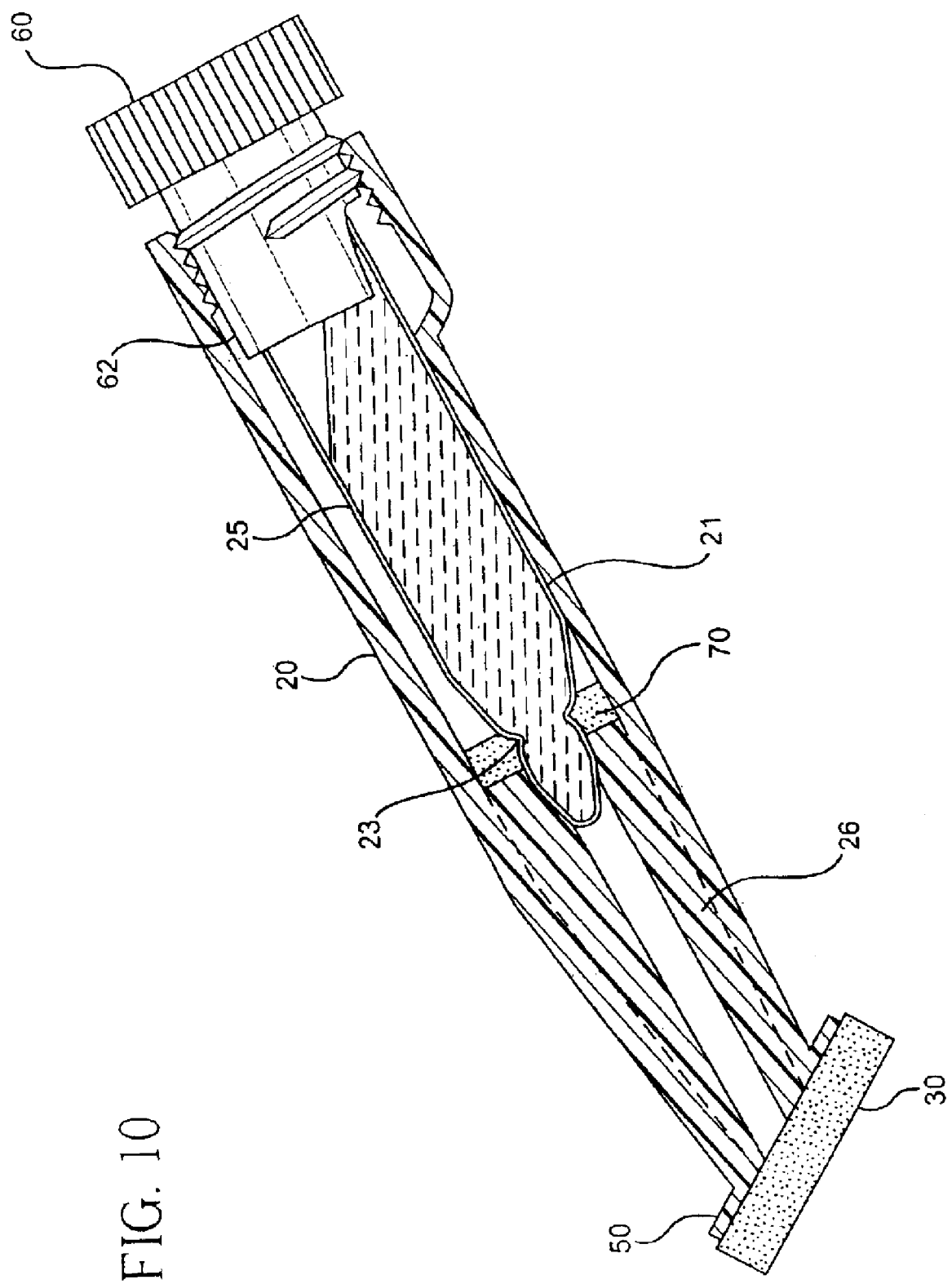
FIG. 10 is a side view of another example of the applicator of the present invention with a rotationally activated back plug prior to activation.

Alternatively, back plug 60 may be rotationally advanced into hollow body 20, as illustrated in FIGS. 9 and 10. This can be accomplished with a threaded or non-threaded interface, as illustrated by the back plugs of FIGS. 11 and 12. Like the axially advanced back plug, the rotationally advanced back plug includes an internal lever mechanism for activating the applicator. Rotational pressure is applied by a user's thumb, fingers or a combination thereof. Rotation causes back plug 60 to advance, thereby causing internal lever mechanism 62 to pivot ampoule 25, thereby breaking the neck 23 of ampoule 25.

Figure 11:
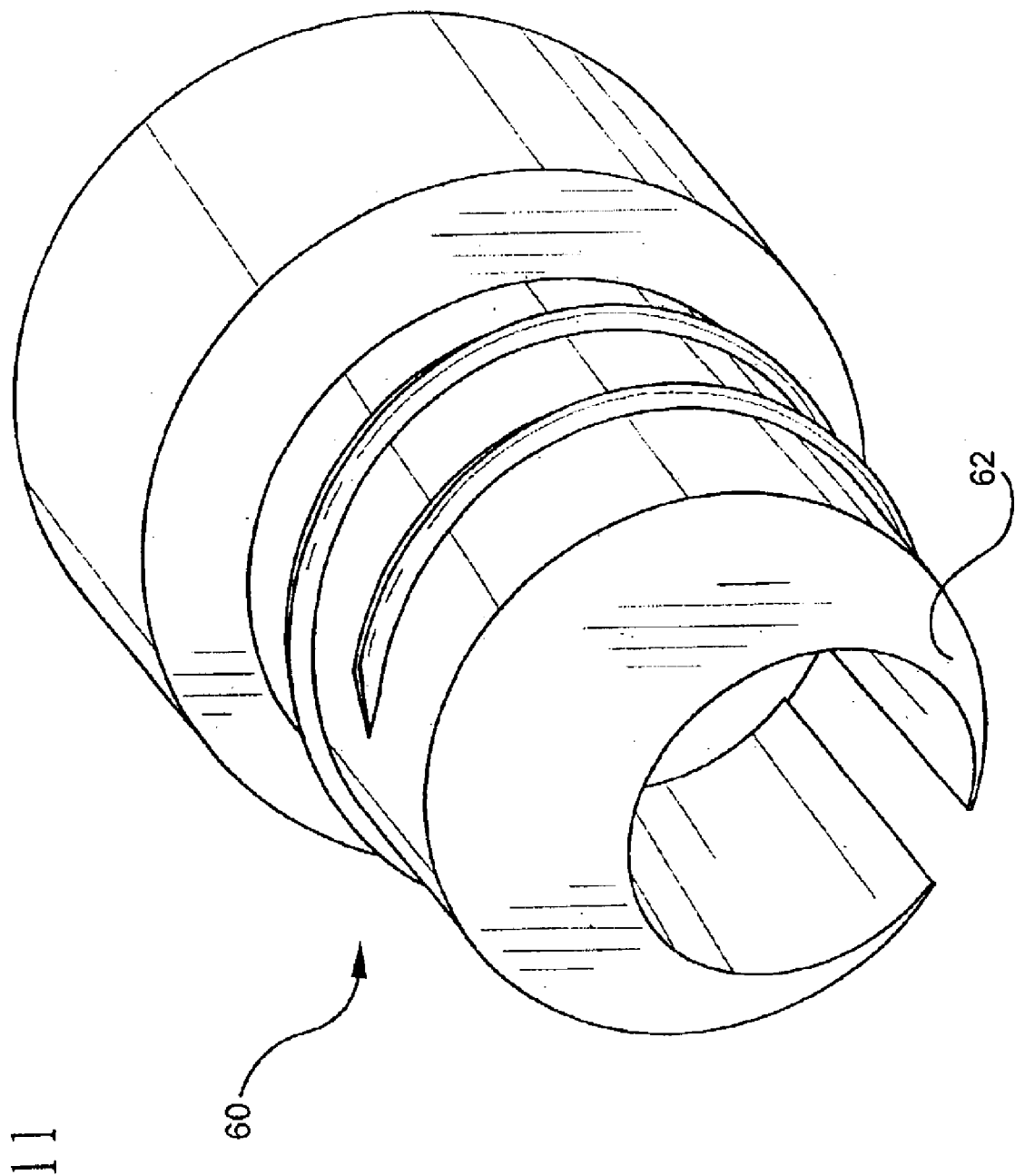
FIG. 11 is a perspective view of an example of a threaded rotational back plug having a concave lever mechanism.
Figure 13:
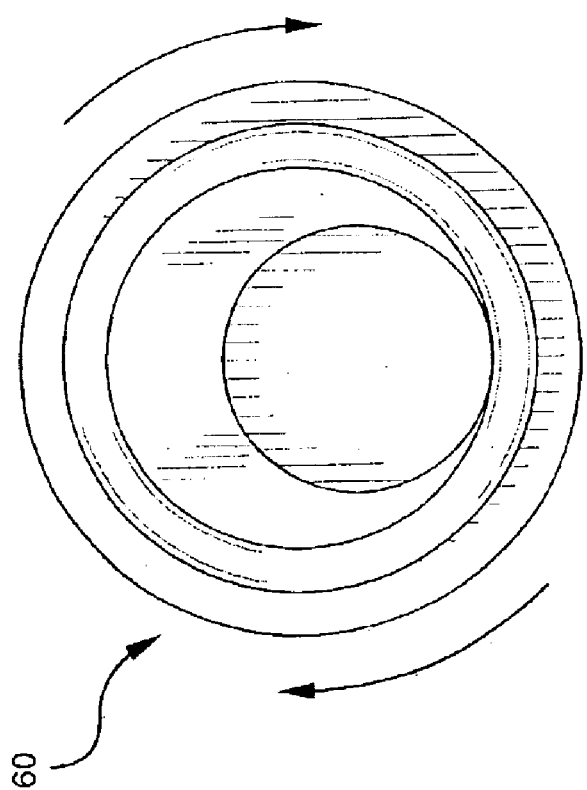
FIG. 13 is a rear view of the back plug of FIG. 11 illustrating rotational direction.
Figure 12:
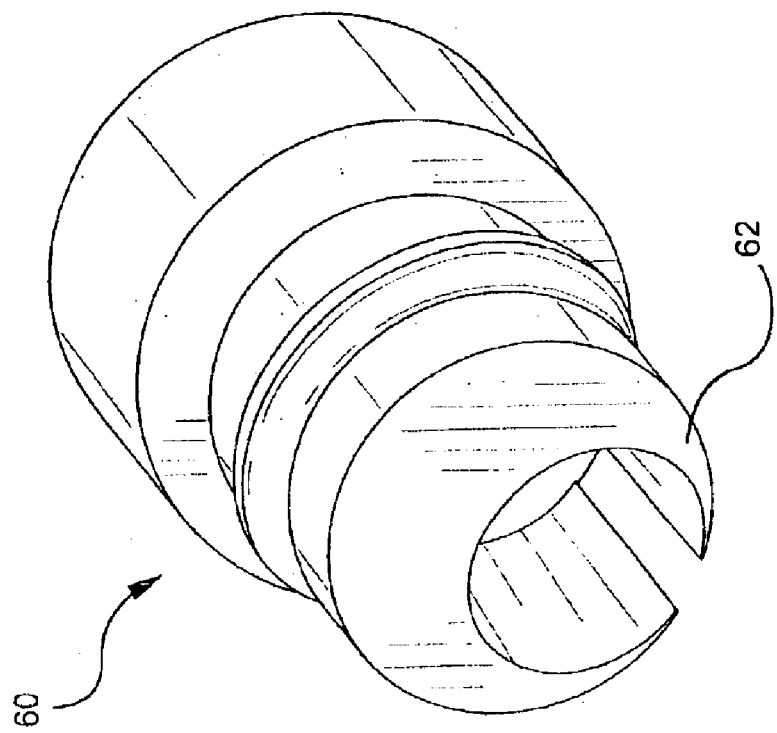
FIG. 12 is a perspective view of a non threaded back plug having a concave lever mechanism.
Figure 15:
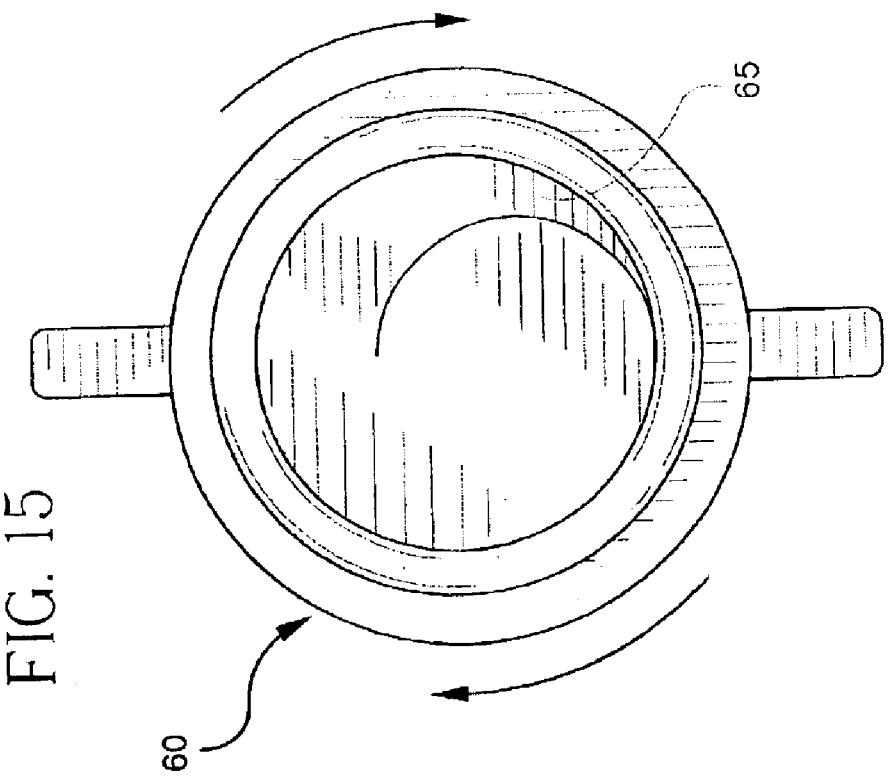
FIG. 15 is a rear view of the back plug of FIG. 14 illustrating rotational direction.

Lever mechanism 62 may include a concave surface to accommodate the end of ampoule 25 and to position ampoule 25 for movement. FIG. 13 illustrates a rear view of back plug 60. As back plug 60 is rotated clockwise, as indicated by the arrows, the concave recess in lever mechanism 62 rotates clockwise to pivot the end of ampoule 25, thereby breaking neck 23. FIG. 11 illustrates a threaded back plug 60; however, back plug 60 may be a non-threaded rotational back plug such as, for example, back plug 60 illustrated in FIG. 12. Unless back plug 60 with lever mechanism 62 is threaded, as illustrated in FIG. 11, the rotational direction may bi-directional.

Figure 14:
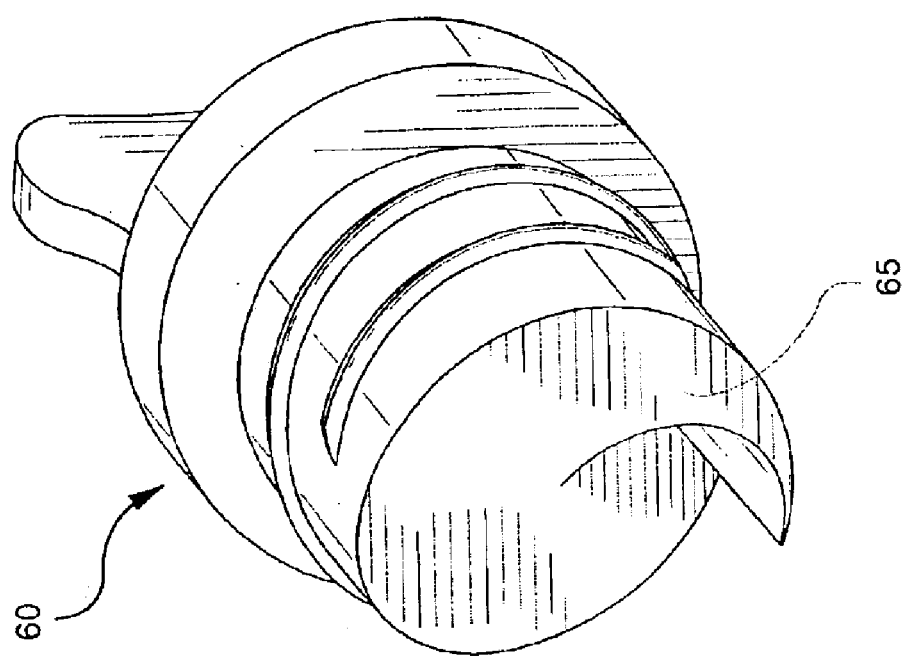
FIG. 14 is a perspective view of a non threaded back plug having an advancing wedge lever mechanism.

In another example of back plug 60, the lever mechanism is an advancing wedge 65, as illustrated in FIG. 14. A tip of advancing wedge 65 is positioned under the end of ampoule 25 and, as back plug 60 is rotated further into applicator 10, an increasingly larger portion of advancing wedge 65 is moved under the end of ampoule 25, applying an increasing upwardly pressure on ampoule 25 to pivot the body of ampoule 25.

Figure 17:
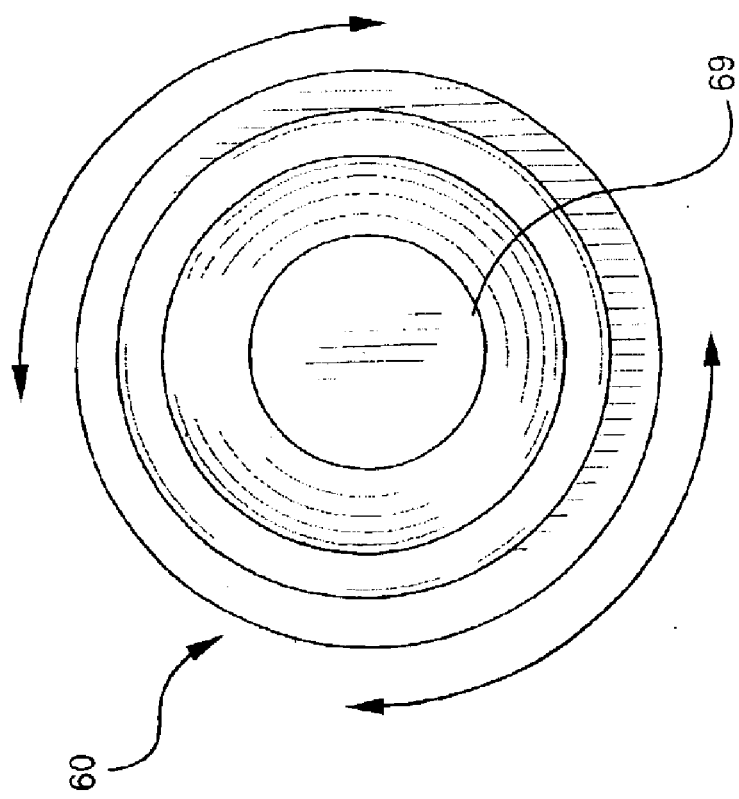
FIG. 17 is a rear view of the back plug of FIG. 16 illustrating rotational direction.
Figure 16:
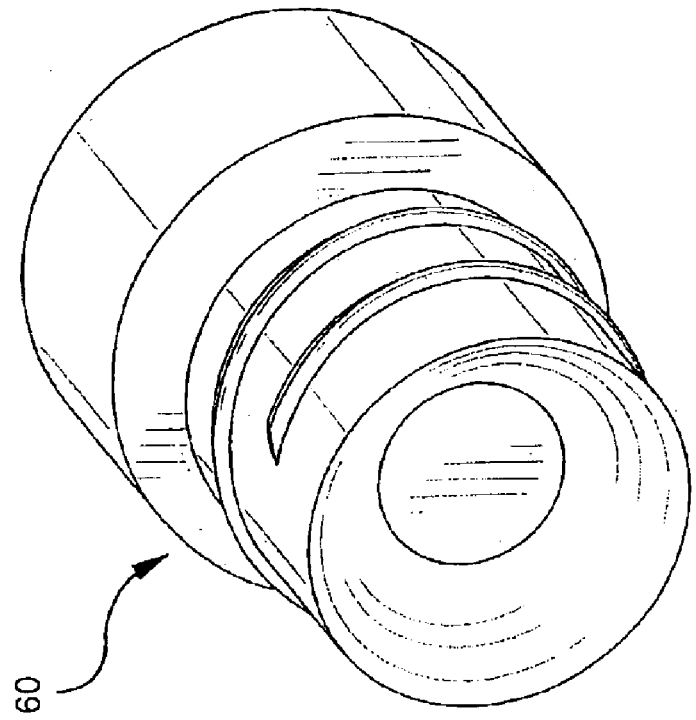
FIG. 16 is a perspective view of a non threaded back plug having an advancing cone lever mechanism.

In yet another example of back plug 60, the lever mechanism is an advancing cone 69, as illustrated in FIGS. 16 and 17. As back plug 60 is rotated further into hollow body 20, ampoule 25 is drawing further into advancing cone 69. The diameter of advancing cone 69 decreases, causing ampoule 25 to pivot vertically, thereby breaking neck 23 of ampoule 25. Unless back plug 60 with advancing cone 69 is threaded, as illustrated in FIG. 16, the rotational direction may bi-directional, as illustrated by the arrows in FIG. 17.

While back plug 60 is illustrated and discussed as having a particular direction of rotation, the rotational direction may be reversed. Those skilled in the art will also appreciate that various configurations described above could be combined with the below described embodiment to form multiple variations of the invention.

Figure 18:
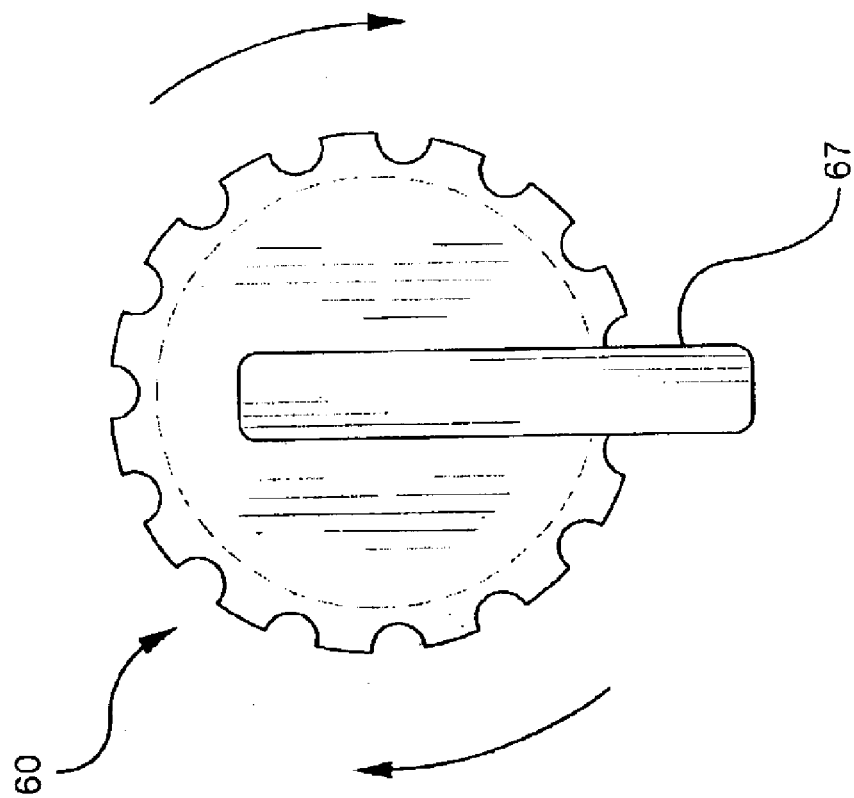
FIG. 18 is a front view of an example of a back plug having a torque bar to facilitate activation of the application of this invention.
Figure 19:
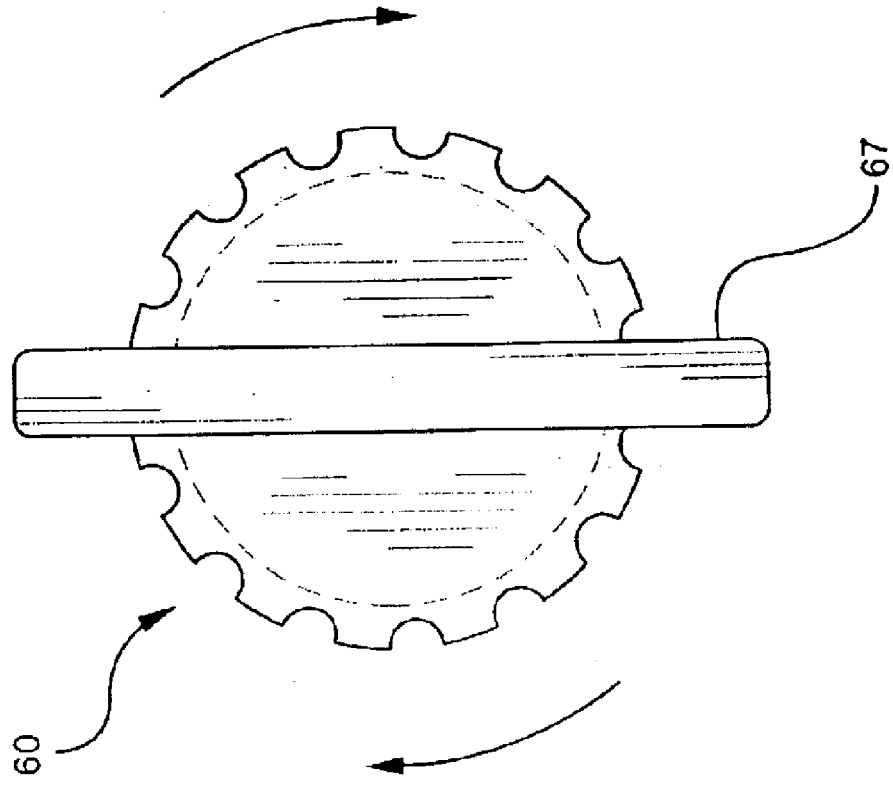
FIG. 19 is a front view of another example of a back plug having a torque bar to facilitate activation of the application of this invention.
Figure 21:
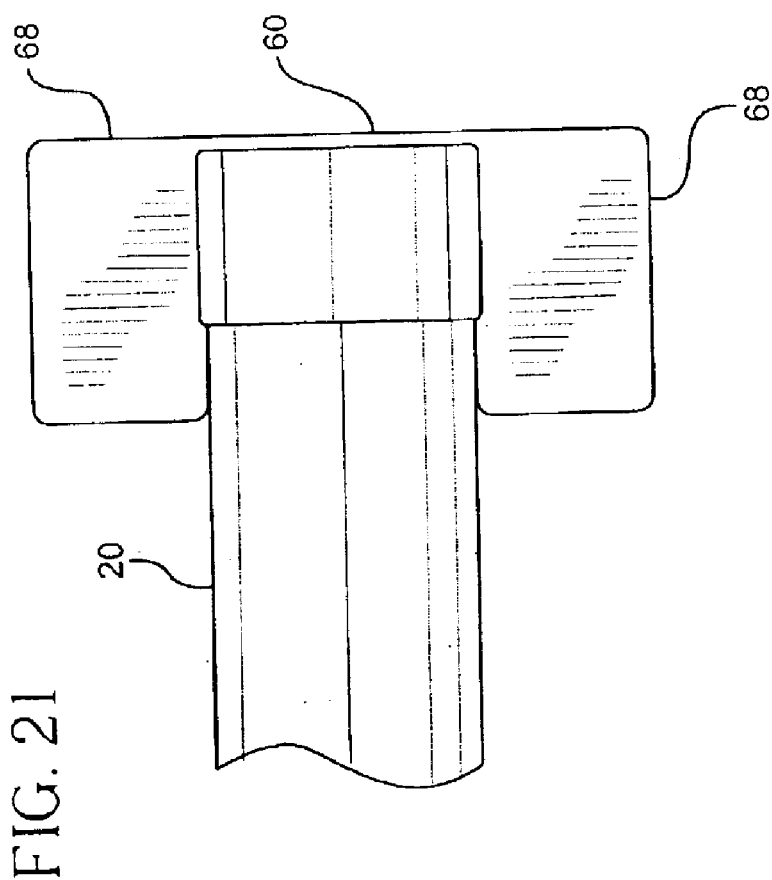
FIG. 21 is a front view of another example of a back plug having wings to facilitate activation of the application of this invention.
Figure 20:
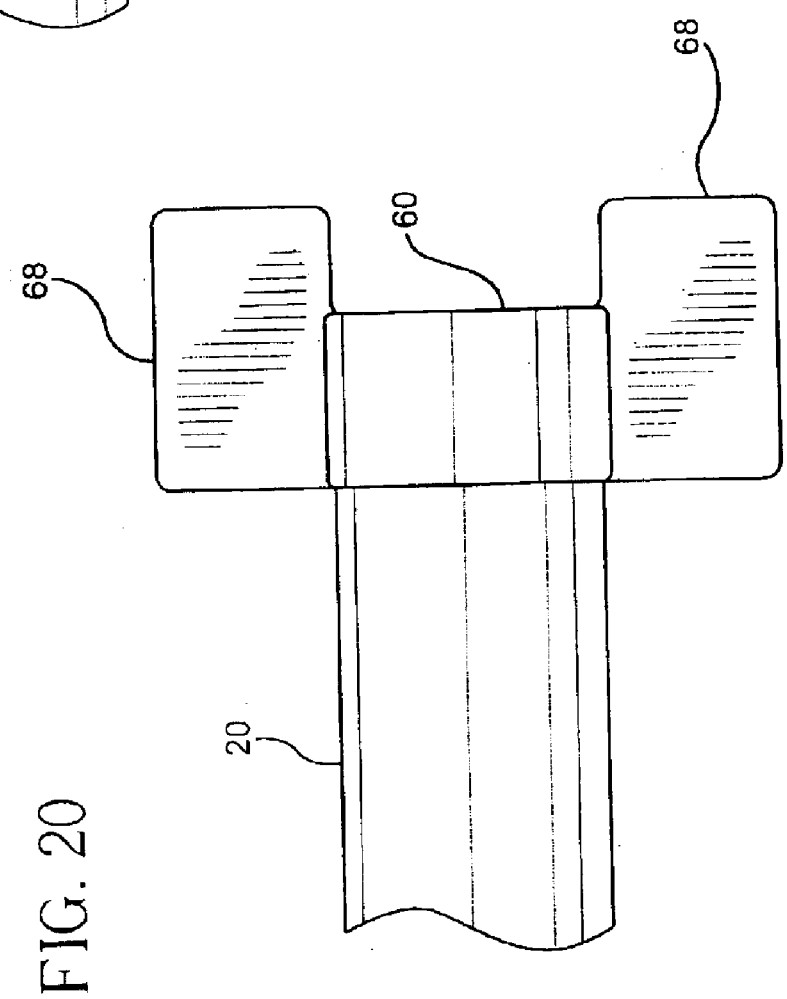
FIG. 20 is a front view of an example of a back plug having wings to facilitate activation of the application of this invention.
Figure 22:
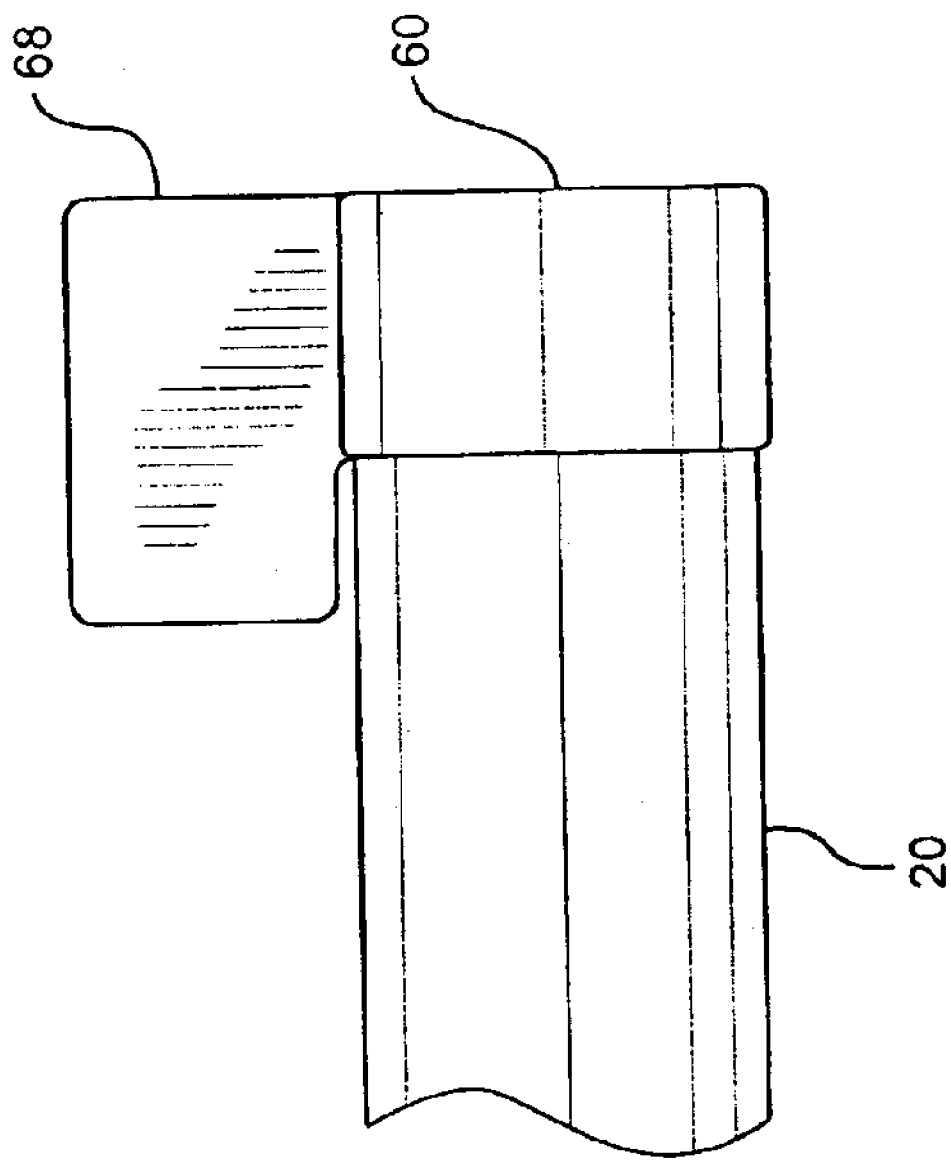
FIG. 22 is a front view of an example of a back plug having a single wing to facilitate activation of the application of this invention.
Figure 23:
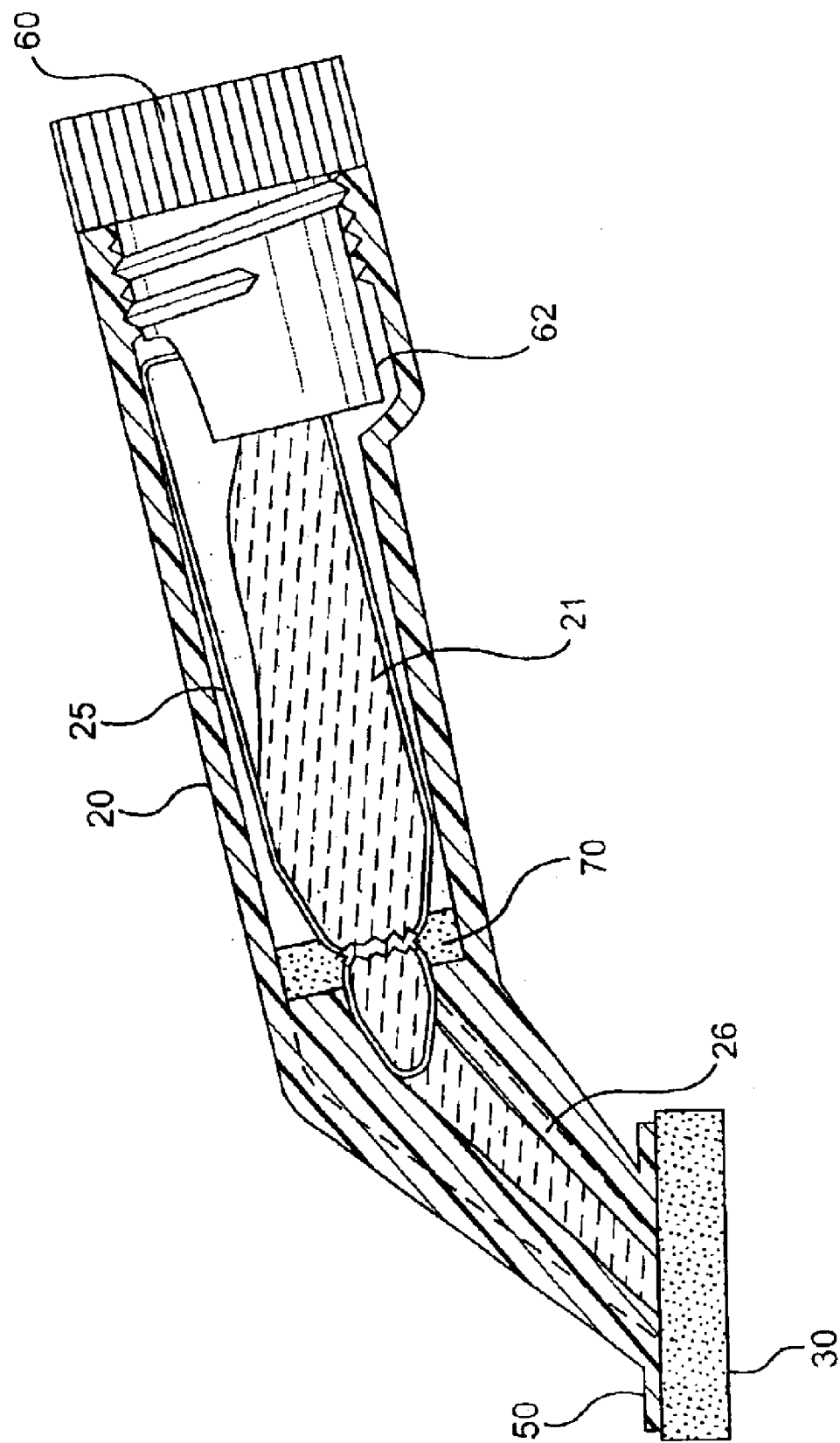
FIG. 23 is a side view of an example of an applicator having a rotational back plug after activation.

Back plug 60 may include a variety of features to facilitate rotation by the clinician to activate applicator 10. Back plug 60 may be configured with a torque bar 67, as illustrated in FIGS. 18 and 19, or wings 68 to facilitate tightening of back plug 60 by finger pressure, as illustrated in FIGS. 20–22. Torque bar 67 is located on the exterior end of back plug 60 extending a distance past one or both sides of back plug 60, as shown in FIGS. 18 and 19. Alternatively, torque bar 67 may include wings 68. Wings 68 may be oriented upwardly, as illustrated in FIG. 20, or downwardly, as illustrated in FIGS. 21 and 22. Back plug 60 may have a single wing or double wings. Alternatively, back plug 60 may include a ribbed other surface along the exterior perimeter, as illustrated in FIG. 23, to allow the clinician to firmly grip back plug 60 for rotational advancement.

The press fit or screw fit (threaded) back plug is inserted into the open proximal end and will act will create a seal after activation. When the back plug is rotational, the thread seals the proximal end, as illustrated in FIG. 23. When back plug 60 is press fit, whether axially advanced or rotationally advanced, sealing of the opening at the proximal end of the applicator by back plug 60 can be accomplished by means of a ring 62 protruding from one of the interior surface of hollow body 20 and back plug 60 with a mating recess in the other one of the interior surface of hollow body 20 and back plug 60. Sealing of the press fit back plug is illustrated in FIG. 24.

Because the area around neck 23 of ampoule 25 is held firmly in place by ribs 26, ampoule 25 pivots vertically upward, thereby breaking the firmly held ampoule neck 23, held in place by ribs 26 running parallel to the applicator hollow body 20. The design of ribs 26 allows the antimicrobial solution to flow after activation and will continue to hold neck portion 23 of ampoule 25 after breaking ampoule 25.

Once activated, highly porous foam ring insert 70 around neck 23 of ampoule 25 promotes liquid flow from ampoule 25, and the spacing between the ribs 26 provides a passage for solution within ampoule 25 to flow to applicator pad assembly 30 at the distal end of applicator 10. The applicator may include a small pinhole through a top wall of hollow body 20 to increase the flow of solution within applicator 10. The hole would be sized to allow airflow but would not allow liquid flow.

Figure 25:
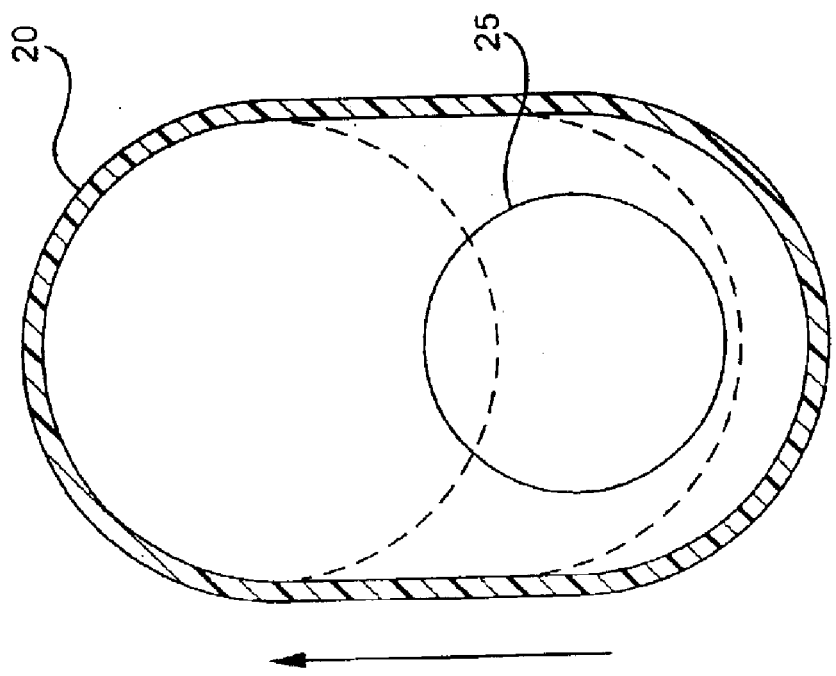
FIG. 25 is a cross sectional view of an ovular hollow body.

Referring now to FIG. 25, there it is shown in a cross sectional view from the proximal end of applicator 10, that hollow body 20 may be ovular in shape to allow movement of ampoule 25 in the vertical direction and to provide a means for aligning an axially advanced back plug 60 to provide the leverage required to move body 21 of ampoule 25 a sufficient distance for activation. Likewise, back plug 60 may be ovular in shape to aid the user in orienting back plug 60 for insertion into hollow body 20. Alternative, the shape of the hollow body 20 and axially activated back plug 60 may be egg-shaped to prevent improper insertion of axially activated back plug 60.

Hollow handle 20 preferably has a generally tubular configuration with an internal configuration to accommodate the sealed ampoule. Preferably, hollow handle 20 is formed from a transparent or translucent polymer such as low, medium or high-density polyethylene, polypropylene, ABS, PET or the like. Because most prep solutions, such as iodine, for example, are colored with a dye or naturally are brown, this feature will allow the clinician to easily determine the amount of antimicrobial solution remaining in hollow handle 20 while in use or during disposal. For user comfort, the applicator of the present invention is preferably designed with a dual angle applicator body. As seen in FIG. 1, the preferred angle of flange 32, which is adhered to applicator pad 30, is approximately 45 degrees from the horizontal; however, the applicator can have many configurations and still practice aspects of the invention. Specifically, in certain implementations the angle could range from approximately 15 degrees to approximately 65 degrees. For additional user comfort, hollow handle 20 may be over-molded with a soft material, such as polyisoprene or the like, that is easily gripped and more comfortable to the clinician.

Figure 26:
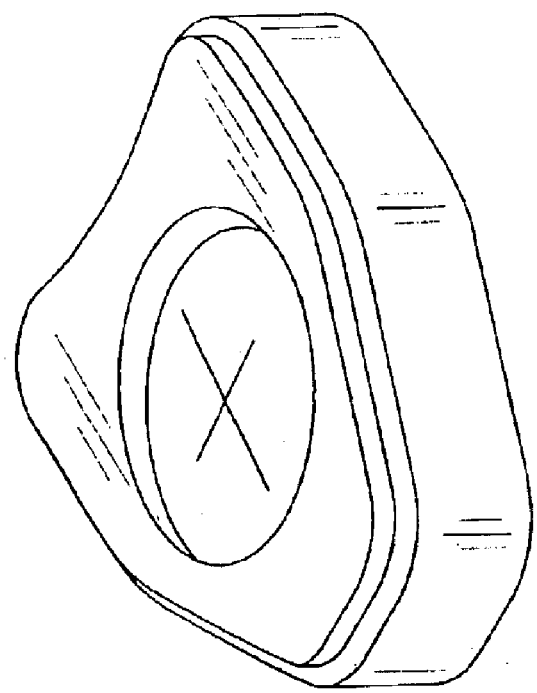
FIG. 26 is a perspective view of an applicator pad used on the applicator of this invention.

Applicator pad 30 is attached to hollow body 20 over the open end of distal portion 24 by adhesive, flame bonding or any other suitable means. In certain applications, the applicator pad may be removably attached to the hollow body. An example of an applicator pad is illustrated in FIG. 26. Applicator pad 30 may be comprised of two or more layers of laminated material. The top layer is preferably a substantially non-porous, hydrophobic material such as polyethylene, polypropylene, silicone or other plastic material. Such material substantially limits the flow of the antimicrobial solution into the bottom layer. Preferably, the bottom layer is open cell foam such as polyurethane or other suitable open cell foam material, that allows the antimicrobial solution to pass therethrough. Alternatively, applicator pad 30 can be formed from a single layer of material. In such a case, the top portion of applicator pad 30 preferably is less porous (more dense) than the bottom portion of applicator pad 30. The varying porosity can be achieved by a number of different techniques. For example, the top portion of applicator pad 30 can be flame treated, or a thin layer of adhesive can be applied over the top portion of applicator pad 30. In addition, applicator pad 30 can be curved so the center of the radius of curvature is located proximally of the top portion of applicator pad 30. This arrangement restricts or closes the open cell structure along the top portion of applicator pad 30. With any of the foregoing techniques, the flow of antimicrobial solution from hollow handle 20 into the bottom portion of applicator pad 30 is reduced.

The face of applicator pad 30 can have any shape desired. For example, applicator pad 30 may have a generally square or rectangular shape, a trapezoidal shape, a shape analogous to home plate in baseball, a circular shape, an elliptical shape or a triangular shape, or any one of the shapes shown in FIGS. 6 through 33 of U.S. Pat. No. 6,371,675, incorporated herein by reference. The foregoing examples are illustrative only and in no way limit the invention.

Figure 28:
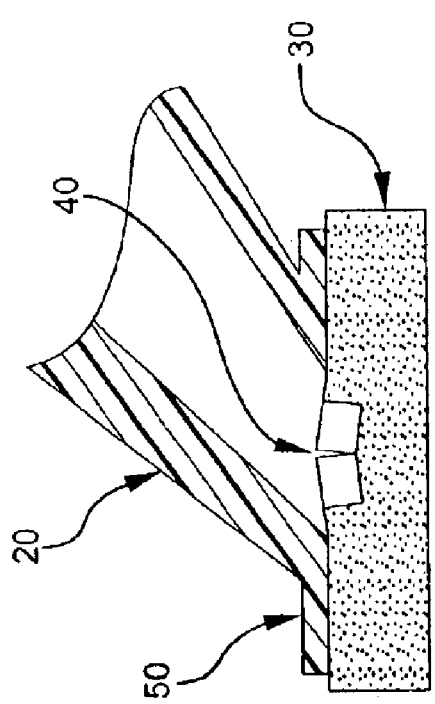
FIG. 28 is a side view of the applicator showing the open view of the slit in the applicator pad connected with the applicator of this invention.
Figure 27:
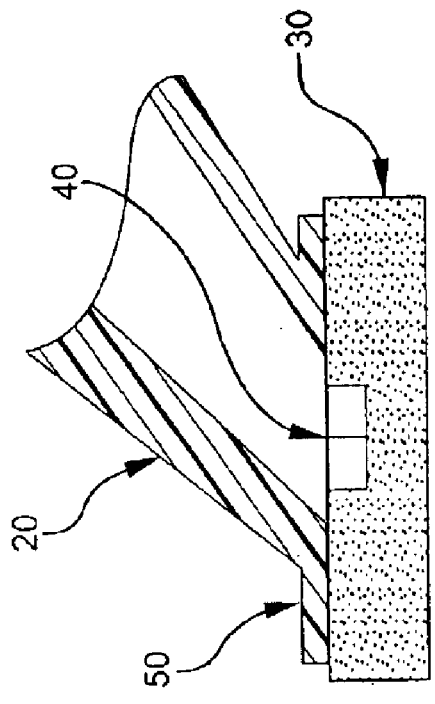
FIG. 27 is a side view of the applicator showing the closed view of the slit in the applicator pad connected with the applicator of this invention.

Applicator pad 30 is formed with a slit 40 therein that acts as a flow control valve to control the flow of the antimicrobial solution from hollow handle 20 to applicator pad 30 and then to the patient. Slit 40 illustrated in FIG. 27 is designed so that it remains closed when no pressure is exerted on the distal surface of applicator pad 30. However, when pressure is exerted on the distal surface of applicator pad 30, such as when applicator 10 is pressed against a patient's skin, slit 40 opens as illustrated in FIG. 28 to allow the antimicrobial solution to flow past slit 40 into applicator pad 30. There the antimicrobial solution can be easily distributed over the patient's skin by applicator pad 30. When a sufficient amount of the antimicrobial solution has flowed into applicator pad 30, the user can release the pressure exerted on the distal surface of applicator pad 30 to stop the flow of antimicrobial solution out of hollow handle 20.

Slit 40 may be a single slit or a plurality of slits and may be in any pattern desired, so long as slit 40 can be used to act as a flow control valve. Exemplary patterns include those shown in FIGS. 6 through 33 of U.S. Pat. No. 6,371,675. Where one slit is used, it is preferably aligned on an axis of the face of applicator pad 30. If a plurality of slits is used, the slits can radiate out in any direction from the center of the face of applicator pad 30. The slits do not have to be straight but may be angled, curved or undulating. Alternatively, the plurality of slits could be formed as a plurality of short single or crossed lines aligned or randomly placed on the face of applicator pad 30. The particular pattern of slits that is used, as well as the density of the pad material, the slit depth and the geometry of the open distal end of hollow handle 20, will affect the rate of flow of the antimicrobial solution. Again, the foregoing examples for the slit pattern are illustrative only and in no way limit the invention.

Slit 40 may extend through only the top layer or the top portion of applicator pad 30, as illustrated in FIG. 35 of U.S. Pat. No. 6,371,675. Alternatively, slit 40 can extend to about the middle of applicator pad 30 so that slit 40 passes through the top layer or the top portion of applicator pad 30 and a part of the bottom layer or the bottom portion of applicator pad 30, as illustrated in FIG. 36 of U.S. Pat. No. 6,371,675. In addition, slit 40 can extend entirely through applicator pad 30, as illustrated in FIG. 37 of U.S. Pat. No. 6,371,675. Where a plurality of slits are used, the depth of penetration of each slit may vary. The depth of penetration will affect the rate of flow of the antimicrobial solution. The slit penetration depth should be approximately to the middle of the applicator pad. This depth ensures that there is adequate flow of the solution while assuring that slit 40 does not open prior to or after use. If the slit penetration depth is too shallow, slit 40 may not open up sufficiently to permit an adequate amount of solution flow. Alternatively, if the slit penetration depth is too great, the distal side of applicator pad 30 may not close appropriately upon removal of pressure on the patient's skin. Again, the foregoing examples are illustrative only and in no way limit the invention.

As discussed above, slit 40 remains closed as long as applicator pad 30 is not pressed onto some surface, such as a patient's skin. In order to ensure that slit 40 remains closed under these circumstances, applicator pad 30 is preferably curved so the center of the radius of curvature is proximal of applicator pad 30. Preferably, this curvature is such that the ends of applicator pad 30 are offset a particular distance from the middle of applicator pad 30 as shown in FIG. 34 of U.S. Pat. No. 6,371,675. This offset distance can be correlated to the thickness of applicator pad 30. Preferably, the curvature of applicator pad 30 is such that the offset distance is between t/6 and t/4 where t is the thickness of the applicator pad. Forming an interface with the desired curvature and then adhering applicator pad 30 to the interface facilitates the provision of the appropriate curvature to applicator pad 30. The curvature of applicator pad 30 also increases patient comfort. This is because applicator pad 30 will move more smoothly over an uneven surface because there is a reduced likelihood that an edge of applicator pad 30 will catch on the patient's skin.

Once applicator pad 30 is pressed onto a patient's skin, slit 40 opens, allowing the antimicrobial solution to flow into the open cells of applicator pad 30. Thereafter, the antimicrobial solution can be dispersed in a controlled manner over the desired patient skin surface area. The application of this flow control technique will greatly reduce the hazard potential when using flammable solution by minimizing the amount of excessive solution and vapors dispensed during a prepping procedure.

Because most prep solutions are colored with a dye or naturally have a brown color, the applicator of the present invention should minimize the likelihood of staining from leakage or dripping of the antimicrobial solution. The flow control feature of this applicator substantially eliminates excess solution from dripping onto the patient or other non-desirable areas. This is a safety and convenience concern.

The applicator of the present invention is compatible with conventional sterilization techniques. A surgical prep applicator is often supplied with a surgical prep kit. These surgical prep kits are often sterilized; therefore, the applicator must be capable of being sterilized with no adverse effects to the applicator's function or strength, or the solutions chemistry, stability or efficacy. Of particular concern is the common use of ETO for this type of sterilization. During the ETO sterilization process, ETO penetrates through polymetric packaging and components. A glass ampoule provides a barrier to ETO during the sterilization process and is, therefore, the best choice for the applicator of the present invention.

Thus, it is seen that an applicator for an antimicrobial prep solution is provided that controls the amount of the solution that flows from the applicator, that allows the user to stop the flow of the solution therefrom when desired and that allows the solution to remain in the applicator after some of the solution has been dispensed for subsequent use or disposal.

It will be apparent that the present invention has been described herein with reference to certain preferred or exemplary embodiments. The preferred or exemplary embodiments described herein may be modified, changed, added to, or deviated from without departing from the intent, spirit and scope of the present invention.

We claim:

1. An applicator comprising:
   a sealed ampoule having a first end, a body and a neck there between, wherein the ampoule contains a soluton;
   an applicator pad;
   an applicator body having an open proximal end and an open distal end adapted to securely hold the first end of the ampoule and to allow movement of the body of the ampoule, wherein the open distal end includes a flange to accept the applicator pad; and
   a back plug having a lever mechanism for insertion into the open proximal end of the rigid applicator body, wherein advancement of the back plug results in a perpendicular force to the longitudinal axis that pivots the body at the ampoule's neck.

2. The applicator of claim 1, further comprising a ring insert within the body approximately around the ampoule neck.

3. The applicator of claim 1, wherein the back plug includes an internal lever mechanism.

4. The applicator of claim 1, wherein the back plug is pivotally connected with the proximal end of the applicator body and wherein the back plug pivotally advances into the open proximal end of the applicator body to activate the applicator.

5. The applicator of claim 1, wherein the back plug is rotationally advanced into the open proximal end of the applicator body.

6. The applicator of claim 5, wherein the back plug includes a lever mechanism and wherein rotational advancement of the back plug into the applicator body rotationally advances the lever mechanism to pivot the body of the ampoule to break the neck and dispense the solution contained therein.

7. The applicator of claim 6, wherein the lever mechanism is a concave surface in one end of the back plug and wherein, as the back plug is rotationally advanced, the concave surface interfaces with an end of the ampoule body pivoting the ampoule body to break the neck.

8. The applicator of claim 6, wherein the lever mechanism is an advancing wedge.

9. The applicator of claim 8, wherein advancement of the back plug into the open proximal end advances the advancing wedge under the body of the ampoule to pivot the body of the ampoule to break the ampoule at the neck.

10. The applicator of claim 6, wherein the lever mechanism is an advancing cone.

11. The applicator of claim 10, wherein rotational advancement of the back plug advances the advancing cone to pivot the body of the ampoule causing the ampoule neck to break.

12. The applicator of claim 5, wherein a rotational direction of the back plug is bi-directional.

13. The applicator of claim 5, wherein the back plug is threaded for advancement into the open proximal end of the applicator body.

14. The applicator of claim 5, further comprising a torque bar connected with the back plug.

15. The applicator of claim 5, wherein the back plug includes a wing extending from an external end of the back plug.

16. The applicator of claim 5, wherein the back plug includes a ribbed surface on the exterior perimeter.

17. The applicator of claim 1, further comprising:
   a protruding ring around one of an exterior perimeter of the back plug and an interior perimeter at the proximal end of the applicator body, and
   a mating ring round the other one of the exterior perimeter of the back plug and the interior perimeter at the proximal end of the applicator body to seal the applicator following activation.

18. An applicator comprising:
   a sealed ampoule having a first end, a body and a neck there between, wherein the sealed ampoule contains a solution;
   an applicator pad;
   a applicator body having an open proximal end and an open distal end, wherein the open distal end includes a flange to accept the applicator pad, and wherein the applicator body accommodates the ampoule, the body comprising:
   a distal portion to firmly hold the first end of the ampoule within the distal portion of the applicator body;
   a handle portion having an interior diameter sufficient to accommodate the body of the ampoule and allow sufficient movement of the body to activate the applicator; and a back plug having a lever mechanism for insertion into the open proximal end of the rigid applicator body, wherein advancement of the back plug results in a perpendicular force to the longitudinal axis that pivots the body of the ampoule to break the neck of the ampoule to dispense the solution contained therein.

19. A method of delivering a solution including:

providing a solution in a breakable, rigid sealed ampoule, the ampoule having a first end, a body and a neck there between;

providing an applicator body having a proximal and a distal end;

positioning the ampoule in the applicator body such that the first end of the ampoule is secured with respect to the applicator body;

providing a back plug at the proximal end of the applicator body; and displacing a back plug having a lever mechanism for insertion into the open proximal end of the rigid applicator body, wherein advancement of the back plug results in a perpendicular force to the longitudinal axis that pivots the body of the ampoule to break its neck.

20. The method of claim 19 wherein an applicator pad at the distal end of the applicator body is comprised of a single layer of material having a selected, varying porosity.

21. The method of claim 19 wherein an applicator pad at the distal end of the applicator body has a bottom and a top, wherein the bottom is more porous than the top.

22. An applicator comprising:

a sealed ampoule having a first end, a body and a neck there between, wherein the ampoule contains a solution;

an applicator pad;

a hollow applicator body comprising internal ribs including a recess there between to allow the solution dispensed from the ampoule to flow into a distal portion of the applicator body and having an open proximal end and an open distal end adapted to securely hold the first end of the ampoule and to allow movement of the body of the ampoule, wherein the open distal end includes a flange to accept the applicator pad and a structure to securely hold the first end of the ampoule within the applicator;

a handle portion having an interior diameter sufficient to accommodate the body of the ampoule and to allow movement of the body of the ampoule to activate the applicator; and a back plug wherein advancement of the back plug into the open proximal end of the applicator body results in a perpendicular force to the longitudinal axis that pivots the body of the ampoule to break the neck.

23. An applicator comprising:

a sealed ampoule having a first end, a body and a neck there between, wherein the ampoule contains a solution;

an applicator pad;

a hollow applicator body having an open proximal end and an open distal end, wherein the open distal end includes a flange to accept the applicator pad and a distal portion having internal ribs to securely hold the first end of the ampoule within the applicator;

a handle portion having an interior diameter sufficient to accommodate the body of the ampoule and to allow movement of the body of the ampoule to activate the applicator; and a back plug wherein advancement of the back plug into the open proximal end of the applicator pivots the body of the ampoule to the neck.

24. The applicator of claim 23, wherein the open proximal end of the applicator body receives the ampoule.

25. The applicator of claim 23, further comprising a structure within the applicator body to firmly hold the first end of the ampoule, wherein the structure allows the solution from the ampoule to flow to the distal end of the applicator body.

26. An applicator comprising:

a sealed ampoule having a first end, a body and a neck there between, wherein the ampoule contains a solution;

an applicator pad;

an applicator body having an open proximal end and an open distal end adapted to securely hold the first end of the ampoule and to allow movement of the body of the ampoule;

wherein a structure within the applicator body comprises of ribs parallel with the applicator body to firmly hold the first end of the ampoule within the applicator body; and an area between the ribs to allow the solution from the ampoule to flow into the distal end of the applicator body;

wherein the structure allows the solution from the ampoule to flow to the distal end of the applicator body; and wherein the open distal end includes a flange to accept the applicator pad; and a back plug having a lever mechanism for insertion into the open proximal end of the rigid applicator body, wherein advancement of the back plug results in a perpendicular force to the longitudinal axis that pivots the body of the ampoule to break the neck.

* * * * *